US011266085B2

(12) United States Patent
Kaplan-Bie et al.

(10) Patent No.: US 11,266,085 B2
(45) Date of Patent: Mar. 8, 2022

(54) INCREASED HOMOGENEITY OF MYCOLOGICAL BIOPOLYMER GROWN INTO VOID SPACE

(71) Applicant: Ecovative Design LLC, Green Island, NY (US)

(72) Inventors: Jessie Hannah Kaplan-Bie, Troy, NY (US); Lucy Elaine Greetham, South Hero, VT (US); Ian Thomas Bonesteel, Wynantskill, NY (US); Gavin Reim McIntyre, Troy, NY (US)

(73) Assignee: ECOVATIVE DESIGN LLC, Green Island, NY (US)

( * ) Notice: Subject to any disclaimer, the term of this patent is extended or adjusted under 35 U.S.C. 154(b) by 0 days.

(21) Appl. No.: 16/190,585

(22) Filed: Nov. 14, 2018

(65) Prior Publication Data

US 2020/0146224 A1    May 14, 2020
US 2021/0127601 A9    May 6, 2021

Related U.S. Application Data

(60) Provisional application No. 62/707,704, filed on Nov. 14, 2017.

(51) Int. Cl.
*A01G 18/69* (2018.01)
*C12M 1/00* (2006.01)
*C12N 1/14* (2006.01)

(52) U.S. Cl.
CPC ............. *A01G 18/69* (2018.02); *C12M 23/00* (2013.01); *C12M 29/06* (2013.01); *C12M 29/24* (2013.01); *C12N 1/14* (2013.01)

(58) Field of Classification Search
CPC .................................................... C12M 23/00
See application file for complete search history.

(56) References Cited

U.S. PATENT DOCUMENTS

| | | | |
|---|---|---|---|
| 1,979,176 A | 10/1934 | Schicht | |
| 2,509,984 A | 5/1950 | Morrow | |
| 2,657,647 A | 11/1953 | Rapisarda | |
| 2,723,493 A * | 11/1955 | Stoller | C05F 17/00 47/1.1 |
| 2,815,621 A | 12/1957 | Carter | |
| 2,964,070 A | 12/1960 | Linhardt | |
| 3,268,606 A | 8/1966 | Jaeger | |
| 3,316,592 A | 5/1967 | Forrest | |
| 3,317,375 A | 5/1967 | Molinet et al. | |
| 3,421,554 A | 1/1969 | Carter | |
| 3,477,558 A | 11/1969 | Fleischauer | |
| 3,499,261 A | 3/1970 | Hullhorst et al. | |
| 3,708,952 A | 1/1973 | Schulze et al. | |
| 3,717,953 A | 2/1973 | Kuhn et al. | |
| 3,782,033 A | 1/1974 | Hickerson | |
| 3,810,327 A | 5/1974 | Giansante | |
| 3,828,470 A | 8/1974 | Stoller | |
| 3,961,938 A | 6/1976 | Iizuka et al. | |
| 4,027,427 A | 6/1977 | Stoller et al. | |
| 4,036,122 A | 7/1977 | Langen | |
| 4,038,807 A | 8/1977 | Beardsley et al. | |
| 4,063,383 A | 12/1977 | Green | |
| 4,073,956 A | 2/1978 | Yates | |
| 4,127,965 A | 12/1978 | Mee | |
| 4,136,767 A | 1/1979 | Sarovich | |
| 4,226,330 A | 10/1980 | Butler | |
| 4,263,744 A | 4/1981 | Stoller | |
| 4,265,915 A | 5/1981 | MacLennan et al. | |
| 4,294,929 A | 10/1981 | Solomons et al. | |
| 4,337,594 A | 7/1982 | Hanacek et al. | |
| 4,370,159 A | 1/1983 | Holtz | |
| 4,568,520 A | 2/1986 | Ackermann et al. | |
| 4,620,826 A | 11/1986 | Rubio et al. | |
| 4,716,712 A | 1/1988 | Gill | |
| 4,722,159 A | 2/1988 | Watanabe et al. | |
| 4,878,312 A | 11/1989 | Shimizu | |
| 4,922,650 A | 5/1990 | Akao et al. | |
| 4,960,413 A | 10/1990 | Sagar et al. | |
| 5,021,350 A | 6/1991 | Jung et al. | |
| 5,030,425 A | 7/1991 | Bowers-Irons et al. | |
| 5,074,959 A | 12/1991 | Yamanaka et al. | |
| 5,085,998 A | 2/1992 | Lebron et al. | |

(Continued)

FOREIGN PATENT DOCUMENTS

| | | |
|---|---|---|
| CN | 1059662 A | 3/1992 |
| CN | 1732887 A | 2/2006 |

(Continued)

OTHER PUBLICATIONS

PhpBB SHOPSMITH Forums, "Cracks in wide paneling boards", Excerpt from Oct. 28, 2017, downloaded from URL <https://www.shopsmith.com/ss_forum/viewtopic.php?p=214601>; 2 pages.
Griffin et al., "Regulation of macromolecular synthesis, colony development and specific growth rate of Achlya bisexualis during balanced growth". J General Microbiol. (1974) 80(2): 381-388.
Haneef et al., "Advanced Materials from Fungal Mycelium: Fabrication and Tuning of Physical Properties", Scientific Reports 7(1): 1-11; DOI: 10.1038/srep41292, Jan. 24, 2017.
Heisig et al., USGS, "Ground-Water Resources of the Clifton Park Area, Saratoga County, New York", 2002, retrieved from the internet (Oct. 15, 2016): http://ny.water.usgs.gov/pubs/wri/wri014104/wrir01-4104.pdf.

(Continued)

*Primary Examiner* — Bin Shen
(74) *Attorney, Agent, or Firm* — Knobbe, Martens, Olson & Bear, LLP

(57) ABSTRACT

The method of growing a biopolymer material employs incubation of a growth media comprised of nutritive substrate and a fungus in containers that are placed in a closed incubation chamber with air flows passed over each container while the chamber is maintained with a predetermined environment of humidity, temperature, carbon dioxide and oxygen. The air flows may be directed parallel or perpendicularly to the surfaces of the growth media.

18 Claims, 13 Drawing Sheets

(56) References Cited

U.S. PATENT DOCUMENTS

| | | |
|---|---|---|
| 5,088,860 A | 2/1992 | Stockdale et al. |
| 5,123,203 A | 6/1992 | Hiromoto |
| 5,230,430 A | 7/1993 | Kidder |
| 5,306,550 A | 4/1994 | Nishiyama et al. |
| 5,335,770 A | 8/1994 | Baker et al. |
| 5,370,714 A | 12/1994 | Ogawa |
| 5,433,061 A | 7/1995 | Hutchinson et al. |
| 5,440,860 A | 8/1995 | Meli et al. |
| 5,475,479 A | 12/1995 | Hatakeyama et al. |
| 5,498,384 A | 3/1996 | Volk et al. |
| 5,503,647 A | 4/1996 | Dahlberg et al. |
| 5,511,358 A | 4/1996 | Morita et al. |
| 5,532,217 A | 7/1996 | Silver et al. |
| 5,569,426 A | 10/1996 | Le Blanc |
| 5,589,390 A | 12/1996 | Higuchi et al. |
| 5,590,489 A | 1/1997 | Hattori et al. |
| 5,598,876 A | 2/1997 | Zanini et al. |
| 5,606,836 A | 3/1997 | Insalaco et al. |
| 5,647,180 A | 7/1997 | Billings et al. |
| 5,681,738 A | 10/1997 | Beelman et al. |
| 5,682,929 A | 11/1997 | Maginot et al. |
| 5,685,124 A | 11/1997 | Jandl |
| 5,711,353 A | 1/1998 | Ichikawa et al. |
| 5,802,763 A | 9/1998 | Milstein |
| 5,854,056 A | 12/1998 | Dschida |
| 5,888,803 A | 3/1999 | Starkey |
| 5,897,887 A | 4/1999 | Haeberli |
| 5,919,507 A | 6/1999 | Beelman et al. |
| 5,944,928 A | 8/1999 | Seidner |
| 5,948,674 A * | 9/1999 | Mankiewicz .......... C05F 17/957 435/290.2 |
| 5,979,109 A | 11/1999 | Sartor et al. |
| 6,041,544 A | 3/2000 | Kananen et al. |
| 6,041,835 A | 3/2000 | Price |
| 6,098,677 A | 8/2000 | Wegman et al. |
| 6,112,504 A | 9/2000 | McGregor et al. |
| 6,197,573 B1 | 3/2001 | Suryanarayan et al. |
| 6,226,962 B1 | 5/2001 | Eason et al. |
| 6,300,315 B1 | 10/2001 | Liu |
| 6,306,921 B1 | 10/2001 | Ghatta et al. |
| 6,329,185 B1 | 12/2001 | Kofod et al. |
| 6,349,988 B1 | 2/2002 | Foster et al. |
| 6,402,953 B1 | 6/2002 | Gorovoj et al. |
| 6,425,714 B1 | 7/2002 | Waddell |
| 6,471,993 B1 | 10/2002 | Shastri et al. |
| 6,475,811 B1 | 11/2002 | Babcock |
| 6,482,942 B1 | 11/2002 | Vittori |
| 6,491,480 B2 | 12/2002 | Waddell |
| 6,500,476 B1 | 12/2002 | Martin et al. |
| 6,523,721 B1 | 2/2003 | Nomoto et al. |
| 6,603,054 B2 | 8/2003 | Chen et al. |
| 6,620,614 B1 | 9/2003 | Lüth et al. |
| 6,660,164 B1 | 12/2003 | Stover |
| 6,679,301 B2 | 1/2004 | Makino et al. |
| 6,726,911 B1 | 4/2004 | Jülich et al. |
| 7,043,874 B2 | 5/2006 | Wasser et al. |
| 7,073,306 B1 | 7/2006 | Hagaman |
| 7,122,176 B2 | 10/2006 | Stamets |
| 7,179,356 B2 | 2/2007 | Aksay et al. |
| 7,395,643 B2 | 7/2008 | Franchini et al. |
| 7,514,248 B2 | 4/2009 | Gower et al. |
| 7,573,031 B2 | 8/2009 | Behar et al. |
| 7,621,300 B2 | 11/2009 | Bonney et al. |
| 7,661,248 B2 | 2/2010 | Conti et al. |
| 7,754,653 B2 | 7/2010 | Hintz |
| 7,836,921 B2 | 11/2010 | Isomura et al. |
| 8,001,719 B2 | 8/2011 | Bayer et al. |
| 8,205,646 B2 | 6/2012 | Isomura et al. |
| 8,227,224 B2 | 7/2012 | Kalisz et al. |
| 8,227,233 B2 | 7/2012 | Kalisz et al. |
| 8,241,415 B2 | 8/2012 | Wantling et al. |
| 8,298,810 B2 | 10/2012 | Rocco et al. |
| 8,313,939 B2 | 11/2012 | Kalisz et al. |
| 8,517,064 B2 | 8/2013 | Isomura et al. |
| 8,658,407 B2 | 2/2014 | Lyons et al. |
| 8,763,653 B2 | 7/2014 | Weigel et al. |
| 8,999,687 B2 | 4/2015 | Bayer et al. |
| 9,079,978 B2 | 7/2015 | Räsänen et al. |
| 9,085,763 B2 | 7/2015 | Winiski et al. |
| 9,253,889 B2 | 2/2016 | Bayer et al. |
| 9,332,779 B2 | 5/2016 | Marga |
| 9,394,512 B2 | 7/2016 | Bayer et al. |
| 9,469,838 B2 | 10/2016 | Schaak et al. |
| 9,485,917 B2 | 11/2016 | Bayer et al. |
| 9,555,395 B2 | 1/2017 | Araldi et al. |
| 9,714,180 B2 | 7/2017 | McIntyre et al. |
| 9,752,122 B2 | 9/2017 | Marga et al. |
| 9,795,088 B2 | 10/2017 | Bayer et al. |
| 9,801,345 B2 | 10/2017 | Bayer et al. |
| 9,803,171 B2 | 10/2017 | Bayer et al. |
| 9,879,219 B2 | 1/2018 | McIntyre et al. |
| 9,914,906 B2 | 3/2018 | Winiski et al. |
| 10,125,347 B2 | 11/2018 | Winiski |
| 10,144,149 B2 | 12/2018 | Araldi et al. |
| 10,154,627 B2 | 12/2018 | McIntyre et al. |
| 10,172,301 B2 | 1/2019 | McNamara et al. |
| 10,266,695 B2 | 4/2019 | Lucht et al. |
| 10,407,675 B2 | 9/2019 | Bayer et al. |
| 10,525,662 B2 | 1/2020 | Bayer et al. |
| 10,537,070 B2 | 1/2020 | Betts et al. |
| 10,583,626 B2 | 3/2020 | Bayer et al. |
| 10,589,489 B2 | 3/2020 | Bayer et al. |
| 10,687,482 B2 | 6/2020 | Ross et al. |
| 10,785,925 B2 | 9/2020 | McNamara et al. |
| 2001/0012235 A1 | 8/2001 | Schuchardt |
| 2002/0110427 A1 | 8/2002 | Waddell |
| 2002/0131828 A1 | 9/2002 | Waddell |
| 2002/0131933 A1 | 9/2002 | Delmotte |
| 2003/0017565 A1 | 1/2003 | Echigo et al. |
| 2003/0056451 A1 | 3/2003 | Pisek et al. |
| 2003/0121201 A1 | 7/2003 | Dahlberg et al. |
| 2003/0232895 A1 | 12/2003 | Omidian et al. |
| 2004/0000090 A1 | 1/2004 | Miller |
| 2004/0020553 A1 | 2/2004 | Amano |
| 2004/0166576 A1 | 8/2004 | Sadaie |
| 2004/0177585 A1 | 9/2004 | Vermette |
| 2005/0133536 A1 | 6/2005 | Kelsey et al. |
| 2005/0137272 A1 | 6/2005 | Gaserod et al. |
| 2006/0134265 A1 | 6/2006 | Beukes |
| 2006/0280753 A1 | 12/2006 | McNeary |
| 2007/0079944 A1 | 4/2007 | Amidon et al. |
| 2007/0196509 A1 | 8/2007 | Riman et al. |
| 2007/0225328 A1 | 9/2007 | Fritz et al. |
| 2007/0227063 A1 | 10/2007 | Dale et al. |
| 2007/0294939 A1 | 12/2007 | Spear et al. |
| 2008/0017272 A1 | 1/2008 | Isomura et al. |
| 2008/0046277 A1 | 2/2008 | Stamets |
| 2008/0047966 A1 | 2/2008 | Carson |
| 2008/0145577 A1 | 6/2008 | Bayer et al. |
| 2008/0234210 A1 | 9/2008 | Rijn et al. |
| 2008/0295399 A1 | 12/2008 | Kawai et al. |
| 2008/0296295 A1 | 12/2008 | Kords et al. |
| 2009/0107040 A1 | 4/2009 | Vandnhove |
| 2009/0191289 A1 | 7/2009 | Lutz et al. |
| 2009/0241623 A1 | 10/2009 | Matano et al. |
| 2009/0246467 A1 | 10/2009 | Delantar |
| 2009/0272758 A1 | 11/2009 | Karwacki et al. |
| 2009/0307969 A1 | 12/2009 | Bayer et al. |
| 2009/0321975 A1 | 12/2009 | Schlummer |
| 2010/0101190 A1 | 4/2010 | Dillon |
| 2010/0158976 A1 | 6/2010 | O'Brien et al. |
| 2010/0159509 A1 | 6/2010 | Xu et al. |
| 2010/0199601 A1 | 8/2010 | Boldrini et al. |
| 2010/0227931 A1 | 9/2010 | Kuwano et al. |
| 2010/0243135 A1 | 9/2010 | Pepper et al. |
| 2010/0326564 A1 | 12/2010 | Isomura et al. |
| 2011/0094154 A1 | 4/2011 | Joaquin |
| 2011/0108158 A1 | 5/2011 | Huwiler et al. |
| 2011/0265688 A1 | 11/2011 | Kalisz et al. |
| 2011/0268980 A1 | 11/2011 | Kalisz et al. |
| 2011/0269209 A1 | 11/2011 | Rocco et al. |
| 2011/0269214 A1 | 11/2011 | Kalisz et al. |
| 2011/0306107 A1 | 12/2011 | Kalisz et al. |
| 2012/0000165 A1 | 1/2012 | Williams |

(56) References Cited

U.S. PATENT DOCUMENTS

| | | |
|---|---|---|
| 2012/0006446 A1 | 1/2012 | Isomura et al. |
| 2012/0060446 A1 | 3/2012 | Merz |
| 2012/0076895 A1 | 3/2012 | Kirejevas et al. |
| 2012/0115199 A1 | 5/2012 | Li et al. |
| 2012/0132314 A1 | 5/2012 | Weigel et al. |
| 2012/0135504 A1 | 5/2012 | Ross |
| 2012/0225471 A1 | 9/2012 | McIntyre et al. |
| 2012/0227899 A1 | 9/2012 | McIntyre et al. |
| 2012/0231140 A1 | 9/2012 | Hofmann et al. |
| 2012/0270031 A1 | 10/2012 | Guan et al. |
| 2012/0270302 A1 | 10/2012 | Bayer et al. |
| 2012/0315687 A1 | 12/2012 | Bayer et al. |
| 2013/0095560 A1 | 4/2013 | McIntyre et al. |
| 2013/0105036 A1 | 5/2013 | Smith et al. |
| 2013/0210327 A1 | 8/2013 | Corominas |
| 2013/0224840 A1 | 8/2013 | Bayer et al. |
| 2013/0274892 A1 | 10/2013 | Lelkes et al. |
| 2013/0309755 A1 | 11/2013 | McIntyre et al. |
| 2014/0038619 A1 | 2/2014 | Moulsley |
| 2014/0056653 A1 | 2/2014 | Scully et al. |
| 2014/0069004 A1 | 3/2014 | Bayer et al. |
| 2014/0093618 A1 | 4/2014 | Forgacs et al. |
| 2014/0173977 A1 | 6/2014 | Juscius |
| 2014/0186927 A1 | 7/2014 | Winiski et al. |
| 2014/0371352 A1 | 12/2014 | Dantin et al. |
| 2015/0033620 A1* | 2/2015 | Greetham ............... A01G 18/00 47/1.1 |
| 2015/0038619 A1 | 2/2015 | McIntyre et al. |
| 2015/0101509 A1 | 4/2015 | McIntyre et al. |
| 2015/0197358 A1 | 7/2015 | Larsen |
| 2015/0342138 A1 | 12/2015 | Bayer et al. |
| 2015/0342224 A1 | 12/2015 | Medoff |
| 2016/0002589 A1 | 1/2016 | Winiski |
| 2016/0264926 A1 | 9/2016 | Winiski et al. |
| 2016/0355779 A1 | 12/2016 | Ross |
| 2017/0000040 A1 | 1/2017 | Bayer et al. |
| 2017/0028600 A1 | 2/2017 | McIntyre et al. |
| 2017/0071214 A1 | 3/2017 | Rehage |
| 2017/0218327 A1 | 8/2017 | Amstislavski et al. |
| 2017/0253849 A1 | 9/2017 | Miller et al. |
| 2017/0253852 A1 | 9/2017 | Bayer et al. |
| 2018/0014468 A1 | 1/2018 | Ross et al. |
| 2018/0148682 A1 | 5/2018 | Ross et al. |
| 2018/0282529 A1 | 10/2018 | Kaplan-Bie |
| 2018/0368337 A1 | 12/2018 | McIntyre et al. |
| 2019/0059431 A1 | 2/2019 | Kozubal et al. |
| 2019/0090436 A1 | 3/2019 | Betts et al. |
| 2019/0284307 A1 | 9/2019 | Chase et al. |
| 2019/0322997 A1 | 10/2019 | Schaak |
| 2019/0330668 A1 | 10/2019 | Kozubal et al. |
| 2019/0338240 A1 | 11/2019 | Carlton et al. |
| 2019/0357454 A1 | 11/2019 | Mueller et al. |
| 2019/0359931 A1 | 11/2019 | Mueller et al. |
| 2019/0390156 A1 | 12/2019 | Bayer et al. |
| 2020/0024577 A1 | 1/2020 | Carlton et al. |
| 2020/0025672 A1 | 1/2020 | Scullin et al. |
| 2020/0055274 A1 | 2/2020 | Bayer et al. |
| 2020/0095535 A1 | 3/2020 | Kozubal et al. |
| 2020/0102530 A1 | 4/2020 | Winiski et al. |
| 2020/0157506 A1 | 5/2020 | Bayer et al. |
| 2020/0208097 A1 | 7/2020 | Winiski |
| 2020/0239830 A1 | 7/2020 | O'Brien et al. |
| 2020/0268031 A1 | 8/2020 | Macur et al. |
| 2020/0270559 A1 | 8/2020 | Macur et al. |
| 2020/0392341 A1 | 12/2020 | Smith et al. |

FOREIGN PATENT DOCUMENTS

| | | |
|---|---|---|
| CN | 101248869 A | 8/2008 |
| CN | 101653081 A | 2/2010 |
| CN | 106947702 A | 7/2017 |
| EP | 0226292 A1 | 6/1987 |
| EP | 1312547 A1 | 5/2003 |
| EP | 2677030 A1 | 12/2013 |
| EP | 2735318 A1 | 5/2014 |
| EP | 2875805 A1 | 5/2015 |
| EP | 2878340 A1 | 6/2015 |
| EP | 2485779 B1 | 2/2018 |
| EP | 3292769 A1 | 3/2018 |
| GB | 142800 A | 1/1921 |
| GB | 1525484 A | 9/1978 |
| GB | 2032456 A | 5/1980 |
| GB | 2165865 A | 4/1986 |
| IN | 358266 B | 7/2020 |
| JP | H03234889 A | 10/1991 |
| JP | H049316 A | 1/1992 |
| JP | 6111510 | 4/2017 |
| KR | 20050001175 A | 1/2005 |
| KR | 101851655 B1 | 4/2018 |
| WO | WO 1999/024555 | 5/1999 |
| WO | WO 2001/087045 | 11/2001 |
| WO | WO 2005/067977 | 7/2005 |
| WO | WO 2008/025122 | 3/2008 |
| WO | WO 2008/073489 | 6/2008 |
| WO | WO 2010/005476 | 1/2010 |
| WO | WO 2012/122092 | 9/2012 |
| WO | WO 2014/031810 | 2/2014 |
| WO | WO 2014/039938 | 3/2014 |
| WO | WO 2014/195641 | 12/2014 |
| WO | WO 2016/149002 | 9/2016 |
| WO | WO 2016/168563 | 10/2016 |
| WO | WO 2017/056059 | 4/2017 |
| WO | WO 2017/120342 | 7/2017 |
| WO | WO 2017/136950 | 8/2017 |
| WO | WO 2017/151684 | 9/2017 |
| WO | WO 2017/205750 | 11/2017 |
| WO | WO 2018/011805 | 1/2018 |
| WO | WO 2018/014004 | 1/2018 |
| WO | WO 2018/064968 | 4/2018 |
| WO | WO 2018/183735 | 10/2018 |
| WO | WO 2018/189738 | 10/2018 |
| WO | WO 2019/046480 | 3/2019 |
| WO | WO 2019/099474 | 5/2019 |
| WO | WO 2019/178406 | 9/2019 |
| WO | WO 2019/217175 | 11/2019 |
| WO | WO 2019/226823 | 11/2019 |
| WO | WO 2019/246636 | 12/2019 |
| WO | WO 2020/023450 | 1/2020 |
| WO | WO 2020/072140 | 4/2020 |
| WO | WO 2020/082043 | 4/2020 |
| WO | WO 2020/082044 | 4/2020 |
| WO | WO 2020/102552 | 5/2020 |
| WO | WO 2020/106743 | 5/2020 |
| WO | WO 2020/176758 | 9/2020 |
| WO | WO 2020/186068 | 9/2020 |
| WO | WO 2020/186169 | 9/2020 |
| WO | WO 2020/237201 | 11/2020 |

OTHER PUBLICATIONS

Instructables, How to Grow Oyster Mushroom Spawn (Low Tech), retrieved from the internet Aug. 19, 2018: http://www.instructables.com/id/1-How-to-Grow-Oyster-Mushroom-Spawn-Low-Tech/.

Zadrazil et al., "Influence of CO2 Concentration on the Mycelium Growth of Three Pleurotus Species", European J. Appl. Microbiol., vol. 1, pp. 327-335 (1975).

International Search Report for PCT/US2018/060983, dated Jan. 24, 2019.

Appels et al., "Hydrophobin gene deletion and environmental growth conditions impact mechanical properties of mycelium by affecting the density of the material", Scientific Reports 8:4703 DOI:10.1038/s41598-018-23171-2, Mar. 16, 2018.

Jones et al., "Leather-like material biofabrication using fungi", Nature Sustainability (2020) https://doi.org/10.1038/s41893-020-00606-1, Sep. 7, 2020.

Howden et al., "The effects of breathing 5% CO2 on human cardiovascular responses and tolerance to orthostatic stress", Experimental Physiology, vol. 89, Issue 4, pp. 465-471, Jun. 23, 2004.

Bartnicki-Garcia, "Cell wall chemistry, morphogenesis, and taxonomy of fungi", Annual Review Microbiol. (1968) 22(1): 87-108.

Cha et al., "Biomimetic synthesis of ordered silica structures mediated by block copolypeptides". Nature (2000) 403(6767): 289-292.

(56) References Cited

OTHER PUBLICATIONS

Dugdale J. "This new surf company is making boards of mushrooms". Blog post—Jun. 25, 2015.
Halseide P., "Cutting brick the safe way". The Aberdeen Group (1988) Publication #M880354 in 2 pages.
Highland Woodworking, "Making Thin Lumber and Veneer Out of Ordinary Boards", Sales Website (2017) in 3 pages.
Holt et al., "Biobased Composition Boards Made from Cotton Gin and Guayule Wastes: Select Physical and Mechanical Properties", Int J Mater Prod Tech. (2009) 36: 104-114.
Islam et al., "Morphology and mechanics of fungal mycelium", Scientific Reports, (2017) 7(1): 1-12.
Kerem et al., "Chemically defined solid-state fermentation of Pleurotus Ostreatus". Enzyme Microbiol Tech. (1993) 15(9): 785-790.
Kokubo et al., "Ca,P-rich layer formed on high-strength bioactive glass-ceramic A-W". J Biomed Mater Res. (1990) 24(3): 331-343.
Koutsoukos et al., "Precipitation of calcium carbonate in aqueous solutions". J Chem Soc., Faraday Trans. 1, Physical Chemistry in Condensed Phases, (1984) 80(5): 1181-1192.
Lu et al., "Theoretical Analysis of Calcium Phosphate precipitation in simulated Body Fluid". Biomaterials (2005) 26(10): 1097-1108—Pre-Pub. Version by Hong Kong University of Science and Technology, Department of Mechanical Engineering, Kowloon; 34 pages.
Molvinger et al., "Porous chitosan-silica hybrid microspheres as a potential catalyst". Chem Mater. (2004) 16(17): 3367-3372.
Monmaturapoj et al., "Influence of preparation method on hydroxyapatite porous scaffolds". Bull Mater Sci. (2011) 34(7): 1733-1737.
Manoli et al., "Crystallization of calcite on chitin". J Cryst Growth, (1997) 182(1-2): 116-124.
Mushroom Source, "Aspen Wood Shavings for Mushroom Cultivation", Website (2015) in 2 pages.
National Institute of Health (NIH/NIBIB), "Tissue Engineering and Regenerative Medicine", Retrieved Sep. 24, 2018 from https://www.nibib.nih.gov/science-education/science-topics/tissue-engineering-and-regenerative-medicine in 13 pages.
Passauer U et al., "Pilze in Höhlen" [Cave Mushrooms]. Denisia (2016) 37: 211-224.
Stewart B., "Concrete Fence Posts: Fact Sheet", Texas Agriculture Extension Service, Texas A & M University (1975) Article L-1368 in 4 pages.
Trinci et al., "II. Unrestricted Growth of Fungal Mycelia", The Mycota—Growth, Differenciation and Sexuality by Wessels et al. [Eds], Springer, Berlin, Heidelberg, (1994) Chapter II: 175-193.
Udawatte et al., "Solidification of xonotlite fibers with chitosan by hydrothermal hot pressing". J Mater Sci. Lttrs. (2000) 45(6): 298-301.
University of Sydney, "Competition Between Fungi". Webpage, accessed Jul. 16, 2014—http://bugs.bio.usyd.edu.au/learning/resources/Mycology/Ecology/competition.shtml in 3 pages.
Varma et al., "Porous calcium phosphate coating over phosphorylated chitosan film by a biomimetic method". Biomaterials (1999) 20(9): 879-884.
Wagner A. "Mycelium Biking—Eco-Design at its Best", Master's Thesis at Lulea University of Technology (2016) in 92 pages.
Woller R. "The Pearl Oyster Mushroom", University of Wisconsin Website (2011) in 2 pages.
Wan-Mohtar et al., "The morphology of Ganoderma lucidum mycelium in a repeated-batch fermentation for exopolysaccharide production", Biotechnology Reports (2016) 11:2-11.
Weaver et al., "The stomatopod dactyl club: a formidable damage-tolerant biological hammer". Science (2012) 336(6086): 1275-1280.
Yamasaki et al., "A hydrothermal hot-pressing method: Apparatus and Application". J Mater Sci Lttrs. (1986) 5(3): 355-356.
Zivanovic et al., "Changes in Mushroom Texture and Cell Wall Composition Affected by Thermal Processing". J Food Service (2004) 69: 44-49.

Agnese et al., "Investigating the Influence of Various Plasticizers on the Properties of Isolated Films of Polyvinyl Acetat". The 37th Annual meeting and Exposition of the Controlled Release Society, Jul. 2010, Portland, OR U.S.A.
Amsellem et al., "Long-term preservation of viable mycelia of two mycoherbicidal organisms". Crop Protection (1999) 18: 643-649.
Angelini et al., "Effect of antimicrobial activity of Melaleuca alternifolia essential oil on antagonistic potential of Pleurotus species against Trichoderma harzianum in dual culture." World J Microbiol Biotech. (2008) 24(2): 197-202.
Antón et al., "PimM, a PAS Domain Positive Regulator of Pimaricin Biosynthesis in *Streptomyces natalensis*." Microbiol. (2007) 153: 3174-3183.
Arshad et al., "Tissue engineering approaches to develop cultured meat from cells: a mini review." Cogent Food & Agriculture (2017) 3(1): 1320814 in 11 pages.
Ashiuchi et al., "Isolation of Bacillus subtilis (chungkookjang), a poly-gamma-glutamate producer with high genetic competence". Appl Microbiol Biotechnol. (2011) 57: 764-769.
Bajaj et al., "Poly (glutamic acid)—An emerging biopolymer of commercial interest". Bioresource Tech. (2011) 102(10): 5551-5561.
Baysal et al., "Cultivation of oyster mushroom on waste paper with some added supplementary materials". Biosource Technology (2003) 89: 95-97.
Begum et al., "Bioconversion and saccharification of some lignocellulosic wastes by Aspergillus oryzae ITCC-4857.01 for fermentable sugar production". Elect J Biotech. (2011) (14)5: 3 in 8 pages.
Belardinelli et al., "Actions of Adenosine and Isoproterenol on Isolated Mammalian Ventricular Myocytes." Circulation Res. (1983) 53(3): 287-297.
Belay et al., "Preparation and Characterization of Graphene-agar and Graphene Oxide-agar Composites." JOAPS (2017) 134(33): 45085.
Binder et al., "Phylogenetic and phylogenomic overview of the Polyporales". Mycologia (Nov.-Dec. 2013) 105(6): 1350-1373.
Blanchette et al., "Fungal mycelial mats used as textile by indigenous people of North America", Mycologia (Feb. 20, 2021) pp. 1-7.
Booth et al., "Potential of a dried mycelium formulation of an indigenous strain of Metarhizium anisopliae against subterranean pests of cranberry." Biocontrol Science and Technology (2000) 10: 659-668.
Bormann et al., "Characterization of a Novel, Antifungal, Chitin-binding Protein from *Streptomyces tendae* Tü901 that Interferes with Growth Polarity." J Bacter. (1999) 181(24): 7421-7429.
Bowman et al., "The structure and synthesis of the fungal cell wall". Bioassays (2006) 28(8): 799-808.
Bružauskaite et al., "Scaffolds and Cells for Tissue Regernation: Different Scaffold Pore Sizes—Different Cell Effects." Cytotechnology (2016) 68(3): 355-369.
Cerimi et al., "Fungi as source for new bio-based materials: a patent review", Fungal Biol Biotechnol. (2019) 6: 17; 10 pgs.
Chai et al., "β-Glucan Synthase Gene Overexpression and β-Glucans Overproduction in Pleurotus ostreatus Using Promoter Swapping". PLoS ONE (2013) 8(4): e61693 in 7 pages.
Chaudhary et al., "Understanding rice hull ash as fillers in polymers: a review". Silicon Chemistry (2002) 1:281-289.
Chi et al., "Can Co-culturing of Two White-rot Fungi Increase Lignin Degradation and the Production of Lignin-degrading Enzymes?" Inter'l Biodeter Biodegrad. (2007) 59(1): 32-39.
Collins English Dictionary, "Mould", retrieved from http://collinsdictionary.com/dictionary/english/mould, archived on Apr. 8, 2015, 3 pages.
Dias et al., "Synthesis and characterization of chitosan-polyvinyl alcohol-bioactive glass hybrid membranes". Biomatter (2011) 1(1): 114-119.
Elleuche et al., "Carbonic anhydrases in fungi". Microbiology (2010) 156: 23-29.
Elsacker et al., "Growing living and multifunctional mycelium composites for large-scale formwork applications using robotic abrasive wire-cutting", Construction Bldg Mater. (2021) 283: 122732 in 16 pages.

(56) References Cited

OTHER PUBLICATIONS

Fleet G.H., "Cell walls". in The Yeasts, by Rose et al. [Eds.] 2nd Edition. vol. 4. London: Academic Press. (1991) pp. 199-277.
Frandsen R.J.N., "A guide to binary vectors and strategies for targeted genome modification in fungi using Agrobacterium tumefaciens-mediated transformation". J Microbiol Methods (2011) 87: 247-262.
Gardening KnowHow, Perlite Soil Info: Learn About Perlite Potting Soil, online at www.gardeningknowhow.com/garden-how-to/soil-fertilizers/perlite-potting-soil.htm downloaded on Dec. 16, 2015., 3 pages.
Glowacki et al., "Bioconjugation of Hydrogen-bonded Organic Semiconductors with Functional Proteins." J Mate Chem. C (2015) 3(25): 6554-6564.
Goodell et al., "Fungal Decay of Wood: Soft Rot-Brown Rot-white Rot". In Development of Commercial Wood Preservatives; Schultz et al. [Ed.] ACS Symposium Series; American Chemical Society, Washington, D.C. (2008), Chapter 2, pp. 9-31.
Google Report, Complete colonization substrate mushroom (2 pages) Jan. 30, 2018., 2 pages.
Google Dictionary Definition "Composite", downloaded on Nov. 21, 2018; 1 page.
Gourmet Mushroom, Inc., "What is Mushroom?" —Mushroom Facts Mushroom Information—Educational & Science Projects (2004). Downloaded from www.gmushrooms.com, on Nov. 27, 2017; 5 pages.
Greetham et al., "Pheotypic characterisation of Saccharomyces sensu stricto to Inhibitory Compounds Released During the Deconstruction of Lignocellulosic Material." 3th International Congress on Yeasts, ICY 2012, Aug. 26-30, Madison, USA; 1 page.
Growers Supply. "Horticultural Coarse Perlite—4 Cubic Fee—Growers Supply". URL: https://growerssupply.com; Growers Supply 2012; www.growerssupply.com/farm/supplies/prod1:gs_growing_mediums:pg111049.html; downloaded Dec. 14, 2020 in 3 pages.
Heinzkill et al., "Characterization of laccases and peroxidases from wood-rotting fungi (family Coprinaceae)." Appl Environ Microbiol. (1998) 64: 1601-1606.
Home Depot "Miracle Gro® Perlite Mix", retrieved from the internet: http://homedepot.com/p/Miracle-Gro-8-pt-Perlite-Mix-74278430/204502291; 2 pages.
Home Depot "Pennington—Fast Acting Gypsum", retrieved from the internet: http://homedepot.com/p/Miracle-Gro-8-pt-Perlite-Mix-74278430/204502291; 2 pages.
Horton et al., "Regulation of Dikaryon-Expressed Genes by FRT1 in the Basidiomycete Schizophyllum commune". Fungal Genet Biol. (1999) 26(1): 33-47.
Hüttner et al., "Recent advances in the intellectual property landscape of filamentous fungi", Fungal Biol Biotechnol. (2020) 7:16; 17 pgs.
Hyde et al., "The amazing potential of fungi: 50 ways we can exploit fungi industrially". Fungal Diversity (2019) 97(1): 1-136.
Kamzolkina et al., "Micromorphological features of Pleurotus pulmonarius (Fr.) Quel, and P. ostreaturs (Jacq.) P. Kumm. Strains in pure and binary culture with yeasts". Tsitologiia (2006) 48(2): 153-160.
Kemppainen et al., "Transformation of the Mycorrhizal Fungus Laccaria Bicolor using Agrobacterium tumefaciens." Bioengin Bugs (2011) 2(1): 38-44.
Kerem et al., "Effect of Mananese on Lignin Degradation by Pleurotus ostreatus during Solid-State Fermentation". Applied and Environmental Microbiology (1993) 59(12): 4115-4120.
Kilaru et al., "Investigating dominant selection markers for Coprinopsis cinerea: a carboxin resistance system and re-evaluation of hygromycin and phleomycin resistance vectors". Curr Genet. (2009) 55: 543-550.
Kim et al., "Current Technologies and Related Issues for Mushroom Transformation." Mycobiology (2015) 43(1): 1-8.
Kotlarewski et al., "Mechanical Properties of Papua New Guinea Balsa Wood." European J Wood Wood Products (2016) 74(1): 83-89.

Kück et al., "New tools for the genetic manipulation of filamentous fungi". Appl Microbiol Biotechnol. (2010) 86: 51-62.
Kües, U., "Life History and Development Processes in the Basidiomycete Coprinus Cinereus." Micro Molecular Biol Rev. (2000) 64(2): 316-353.
Kuhar et al., by Ingredi Potassium Sorbate vs Campden Tablets in Wine Making; Jun. 4, 2018. [online]; Retrieved from the Internet <URL: https://ingredi.com/blog/potassium-sorbate-vs-campden-tables-in-wine-making/>; 2 pages.
Kuo, 2005-2006. Glossary of Mycological Terms. Mushroom Expert. Com., pp. 1-13; downloaded from http://www.mushroomexpert.com/glossary.html (May 8, 2015).
Li et al., "Preparation and Characterization of Homogeneous Hydroxyapatite/Chitosan Composite Scaffolds via In-Situ Hydration". J Biomaterials Nanobiotech. (2010) 1: 42-49.
Luo et al., "Coprinus comatus: a basidiomycete fungus forms novel spiny structures and infects nematode." Mycologia (2004) 96(6): 1218-1225.
McPherson et al., "Dissolvable Antibiotic Beads in Treatment of Periprosthetic Joint Infection and Revision Arthroplasty: The Use of Synthetic Pure Calcium Sulfate (Stimulan®) Impregnated with Vancomycin & Tobramycin." Reconstructive Review (2013) 3(1) 12 pages.
Merriam-Webster, "Chamber" dictionary definition; https://www.merriam-webster.com/dictionary accessed Jul. 10, 2017; in 4 Pages.
Merriam-Webster, "pack" Thesaurus definition; https://www.merriam-webster.com/thesaurus; synonyms accessed Aug. 19, 2019; in 10 Pages.
Michielse et al., "Agrobacterium-mediated Transformation of the Filamentous Fungus Aspergillus Awamori." Nature Protocols (2008) 3(10): 1671-1678.
Mitchell et al., [Eds.] "Solid-State Fermentation Bioreactors." Springer Verlag, Berlin/Heidelberg (2006); TOC in 12 Pages.
Moore D., "Fungal Morphogenesis." Cambridge University Press, Cambridge, UK; (1998) TOC in 8 Pages.
Moore D., "Tolerance of Imprecision in Fungal Morphogenesis." In Proceedings of the 4th Meeting on the Genetics and Cellular Biology of Basidiomycetes (Mar. 1998) pp. 13-19.
Mushroom Growers' Handbook 1, "Oyster Mushroom Cultivation". Part II, Chapter 5, (2005) pp. 75-85.
Mushroom Growers' Handbook 2, "Shiitake Bag Cultivation", Part I Shiitake. Published by Mush World (2005) Chapter 4, pp. 73-90 and pp. 105-109.
Naknean et al., "Factors Affecting Retention and Release of Flavor Compounds in Food Carbohydrates." Inter'l Food Res J. (2010) 17(1): 23-34.
Newaz et al., "Characterization of Balsa Wood Mechanical Properties Required for Continuum Damage Mechanics Analysis." Proceedings of the Institution of Mechanical Engineers, Part L: Journal of Materials: Design and Applications (2016) 230(1): 206-218.
Norvell L., Fungi Biology. Encyclopedia.(2002); 2 pages.
Novoselova et al., "Cocultivation of Pleurotus ostreatus (Jacq.) P. Kumm, with yeasts". Moscow University Biol Sciences Bulletin (2011) 66(3): 102-105.
Nussinovitch "Polymer Macro-and Micro-Gel Beads: Fundamentals and Applications", DOI 10.1007/978-1-4419-6618_2, Springer Science & Business Media LLC (2010) TOC in 8 Pages.
Paz et al., "One Step Contruction of Agrobacterium-Recombination-ready-plasmids (OSCAR): An Efficient and Robust Tool for ATMT Based Gene Deletion Construction in Fungi." Fungal Gen Biol. (2011) 48(7): 677-684.
Peksen et al., "Favourable Culture Conditions for mycelial growth of Hydnum repandum, a medicinal mushroom." African Journal of Traditional, Complementary and Alternative Medicines (2013) 10(6): 431-434.
Peng et al., "Microbial biodegradation of polyaromatic hydrocarbons". FEMS Microbiol Rev. (2008) 32:927-955.
Perez et al., "Myxococcus xanthus induces actinorhodin overproduction and aerial mycelium formation by Streptomyces coelicolor." Microbial Biotech. (2011) 4(2): 175-183.
Philippoussis et al., "Production of Mushrooms Using Agro-Industrial Residues as Substrates", in Biotechnology for Agro-Industrial Residues, Chapter 9, (2009) pp. 163-187.

(56) References Cited

OTHER PUBLICATIONS

Poppe J., Mushroom Growers' Handbook 1, 2004, Part II. Chapter 5, "Substrate", pp. 80-81.

Pompei et al., "The Use of Olive Milling Waste-Water for the Culture of Mushrooms on Perlite". Acta Horticulturae (1994) 361:179-185.

Rai et al., "Production of Edible Fungi", in Fungal Biotechnology in Agricultural, Food, and Environmental Applications, D.K. Arora [Ed.], Marcel Dekker, Inc., (2003), Chapter 21, pp. 383-404.

Ross, P., "Pure Culture" 1997-Present; URL: <http://billhoss.phpwebhosting.com/ross/index.php?kind>; downloaded Dec. 14, 2016 in 11 pages.

Royse et al., "Influence of substrate wood-chip particle size on shiitake (Lentinula edodes) yield". Bioresource Tehnology (2001) 76(3): 229-233.

Sapak et al., "Effect of endophytic bacteria on growth and suppression of Tganoderma infection in oil palm". Int J Agric Biol. (2008) 10(2): 127-132.

Schaner et al., "Decellularized Vein as a Potential Scaffold for Vascular Tissue Engineering." J Vascular Surg. (2004) 40(1): 146-153.

Schirp et al., "Production and characterization of natural fiber-reinforced thermoplastic composites using wheat straw modified with the fungus Pleurotus ostreatus". J Appl. Polym Sci. (2006) 102:5191-5201.

Scholtmeijer et al., "Effect of introns and AT-rich sequences on expression of the bacterial hygromycin B resistance gene in the basidiomycete Schizophyllum commune". Appl Environ Microbiol. (2001) 67(1): 481-483.

Schuurman J., "Unique agar Pearls." YouTube video; Feb. 16, 2012, <https://www.youtube.com/watch?v=8GqTTOHETPQ>; 1 page.

Science Daily, May 7, 2007, retrieved from the Internet; http://www.sciencedaily.com/releases/2007/05/070506085628.htm., 3 pages.

Seamon K.B., "Forskolin: Unique Diterpene Activator of Adenylate Cyclase in Membranes and in Intact Cells." PNAS (1981) 78(6): 3363-3367.

Sinotech et al., (2015): retrieved from the Internet http://www.sinotech.com/compressionAndTransferMolding.html., 4 pages.

Slater, M. "Young SoRo Entrepreneur Develops Environmentally Friendly Insulation." The Herald of Randolph. Jun. 21, 2007, pp. 1-2.

Staib et al., "Differential expression of the NRG1 repressor controls species-specific regulation of chlamydospore development in Candida albicans and Candida dubliniensis." Molecular Microbiol. (2005) 55(2): 637-652.

Stamets P., "Mycelium Running". Ten Speed Press (2005); pp. 18, 56, 58, 59, 85, 149, 157, 160 and 291 only.

Stanev et al., "Open Cell Metallic Porous Materials Obtained Through Space Holders. Part I: Production Methods, A Review". JMSE (2016) 139(5): 21 pages.

Stephens et al., "Bringing Cultured Meat to Market: Technical, Socio-political, and Regulatory Challenges in Cellular Agriculture." Trends in Food Science & Technology (2018) 78:155-166.

Sundari et al., "Freeze-drying vegetative mycelium of Laccaria fraterna and its subsequent regeneration". Biotechnology Techniques (1999) 13: 491-495.

Tartar et al., "Differential expression of chitin synthase (CHS) and glucan synthase (FKS) genes correlates with the formation of a modified, thinner cell wall in in vivo-produced Beauveria bassiana cells." Mycopathologia (2005) 160(4): 303-314.

Téllez-Jurado et al., "Expression of a heterologous laccase by Aspergillus niger cultured by solid-state and submerged fermentations." Enzyme Microbial Tech. (2006) 38(5): 665-669.

Téllez-Téllez et al., "Growth and laccase production by Pleurotus ostreatus in submerged and solid-state fermentation." Appl Microbiol Biotechnol. (2008) 81(4): 675-679.

Thomas et al., "Growing Orchids in Perlite". In *Perlite Plant Guide*, The Schundler Company 1951, pp. 1-6, downloaded from http://www.schundler.com/index.html, archived on May 11, 2015.

Timberpress—"How Do Mushrooms Grow So Quickly.", downloaded from the internet: www.timberpress.com/blog/2017/01/how-do-mushrooms-grow-so-quickly, download Feb. 27, 2018 in 7 Pages.

Ugalde U., "Autoregulatory Signals in Mycelial Fungi" in The Mycota: A Comprehensive Treatise on Fungi as Experimental Systems for Basic and Applied Research. K. Esser [Ed.] Springer Publisher, 2nd Edition (2006) Chapter 11; pp. 203-213.

Universal Oil Field, "Sawdust", downloaded from universaloilfield.org on Aug. 23, 2018, 4 pages.

Vara et al., "Cloning and expression of a puromycin N-acetyl transferase gene from Streptomyces alboniger in Streptomyces lividans and Escherichia coli". Gene (1985) 33(22): 197-206.

Visser et al., "Pseudoxylaria as stowaway of the fungus-growing termite nest: Interaction asymmetry between Pseudoxylaria, Termitomyces and free-living relatives". Fungal Ecology (2011) 4(5): 322-332.

Volk (2003) "Tom Volk's Fungus of the Month for Oct. 1998". This month's fungus is Pleurotus ostreatus; the Oyster mushroom, pp. 1-4, downloaded from http://botit.botany.wisc.edu/toms_fungi/oct98.html on May 8, 2015.

Wang et al., "Influence of fungal elicitors on biosynthesis of natamycin by Streptomyces natalensis HW-2". Appl Microbiol Biothechnol. (2003) 97: 5527-5534.

Wikipedia, "Water gel (plain)", Wikipedia Contributors downloaded Aug. 21, 2017 in 1 Page.

Wikipedia, "Wood", downloaded on Nov. 26, 2018, 1 page.

Xiao et al., "A Water-soluble Core Material for Manufacturing Hollow Composite Sections." Comp. Structures (2017) 182: 380-390.

Yang et al., "Medicinal Mushroom Ganoderma lucidum as a Potent Elicitor in Production of t-Resveratrol and t-Peceatannol in Peanut Calluses". J Agric Food Chem. (2010) 58(17): 9518-9522.

Zimin et al., "The MaSuRCA genome assembler". Bioinformatics (2013) 29(21): 2669-2677.

Grant, James. J.—"An investigation of the airflow in mushroom growing structures, the development of an improved, three-dimensional solution technique for fluid flow and its evaluation for the modelling of mushroom growing structures", Doctoral Thesis Sep. 2002; 326 pages.

Antinori et al., "Advanced mycelium materials as potential self-growing biomedical scaffolds." Scientific reports (2021) 11(1): 1-14.

Hidayat et al., "Characterization of polylactic acid (PLA)/kenaf composite degradation by immobilized mycelia of Pleurotus ostreatus". Inter Biodeter Biodegrad. (2012) 71: 50-54.

Jiang et al., "Bioresin Infused then Cured Mycelium-based Sandwich-structure Biocomposites: Resin Transfer Molding (RTM) Process, Flexural Properties, and Simulation." J Cleaner Production (2019) 207:123-135.

Jones et al., Chitin-chitosan Thin Films from Microbiologically Upcycled Agricultural By-products. In 13th International Conference on the Mechanical Behavious of Materials, Melbourne, Australia (Jun. 2019) p. 66; in 7 pages.

Williams, J. "Growth Industry", Financial Times Jan. 12, 2019 (Mogu—Radical by Nature); download from URL <: https://mogu.bio/growth-industry-financial-times-uk-article/> in 1 page.

Wösten et al., "Growing Fungi Structures in Space", ACT Research Category/Space Architecture; Noordwijk, The Netherlands (Oct. 15, 2018) in 17 pages.

Meyer et al., "Comparison of the Technical Performance of Leather, Artificial Leather, and Trendy Alternatives." Coatings (Feb. 2021) 11(2): 226; 14 pages.

Abbadi et al., "Immunocytochemical identification and localization of lipase in cells of the mycelium of Penicillium cyclopium variety", Applied Microbial Cell Physiology (1995) 42: 923-930.

Ando et al., "Cosmetic material for skin whitening - contains mushroom mycelium cultured matter and e.g. ginseng extract, chondroitin sodium sulphate and/or hyaluronic acid", WPI/Thomson (Jan. 14, 1992), 1992(8): Accession #1992-062018; Abstract of JP4009316A; in 9 pages.

Attias et al.., "Biofabrication of Nanocellulose-Mycelium Hybrid Materials", Adv Sustainable Syst. (2020) 5(2): 2000196 in 12 pages; Supporting Information in 7 pages.

(56) References Cited

OTHER PUBLICATIONS

Borrás et al., "Trametes versicolor pellets production: Low-cost medium and scale-up", Biochem Eng J. (2008) 42(1): 61-66.

Green et al., "Mechanical Properties of Wood", Forest Products Laboratory, 1999. in Wood Handbook—Wood as an engineering material. Gen Tech. Rep. FPL-GTR-113, Chapter 4 in 46 pages.

Holt et al. "Fungal mycelium and cotton plant materials in the manufacture of biodegradable molded packaging material: Evaluation study of select blends of cotton byproducts." J Biobased Mater Bioenergy (2012) 6(4): 431-439.

Jiang et al., "Manufacturing of Natural Composites with a Mycelium Binder and Vacuum-infused Vegetable Oil-based Resins", Poster dated May 2014; 1 page.

Jiang et al., "Vacuum Infusion of Mycelium-Bound Biocomposite Preforms with Natural Resins", CAMX ExpoConference Proceedings, Oct. 13-16, 2014, 13 pages.

Jones et al., "Mycelim Composites: A Review of Engineering Characteristics and Growth Kinetics", J Bionanoscience (2017) 11 (4): 241-257.

Jones et al., "Waste-derived Low-cost Mycelium Composite Construction Materials with Improved Fire Safety", FAM (Fire and Materials) (2018) 42(7): 816-825.

Kuhn et al., [Eds.] Cell Walls and Membranes in Fungi—An Introduction (Abstract) in Biochemistry of Cell Walls and Membranes in Fungi, Chapter 1, Springer Verlag Berlin/Heidelberg 1990, 2 pages.

Pathway-27, "Beta-glucan", Aug. 2012, retrieved from http://http://www.pathway27.eu/topstory/beta-glucan/on Oct. 7, 2021 in 2 pages.

Stamets P., "Growing Gourmet and Medicinal Mushrooms", (1993) Chapter 21; p. 363. (Best Available Copy).

Vetchinkina et al., "Bioreduction of Gold (III) Ions from Hydrogen Tetrachloaurate..." Scientific Practical J Health Life Sciences No. 4, ISSN 22188-2268, (2013) pp. 51-56.

Wosten et al., "How a fungus escapes the water to grow into the air", Current Biology. (1999) 9(2): 85-88.

Zeng Z., "Cosmetic composition for cleaning skin, comprises glossy ganoderma spores and collagens, content of glossy ganoderma spores in composition and content of collagens in composition", WPI/Thomson (Feb. 5, 2006) 7: Accession #2007-057767; Abstract of CN1732887A; in 11 pages.

Ziegler et al., "Evaluation of Physico-mechanical Properties of Mycelium Reinforced Green Biocomposites Made from Cellulosic Fibers", Appl Engin Agricult. (2016) 32(6): 931-938.

Collins English Dictionary, "Cavity", Definition; retrieved on Nov. 8, 2021; 1 page.

Merriam-Webster, "desiccated" (Adj.) Definition; downloaded on Nov. 8, 2021; 1 page.

Wang et al., "Chemical and structural factors influencing enzymatic saccharification of wood from aspen, birch and spruce". Biomass Bioengin. (2018) 109: 125-134.

\* cited by examiner

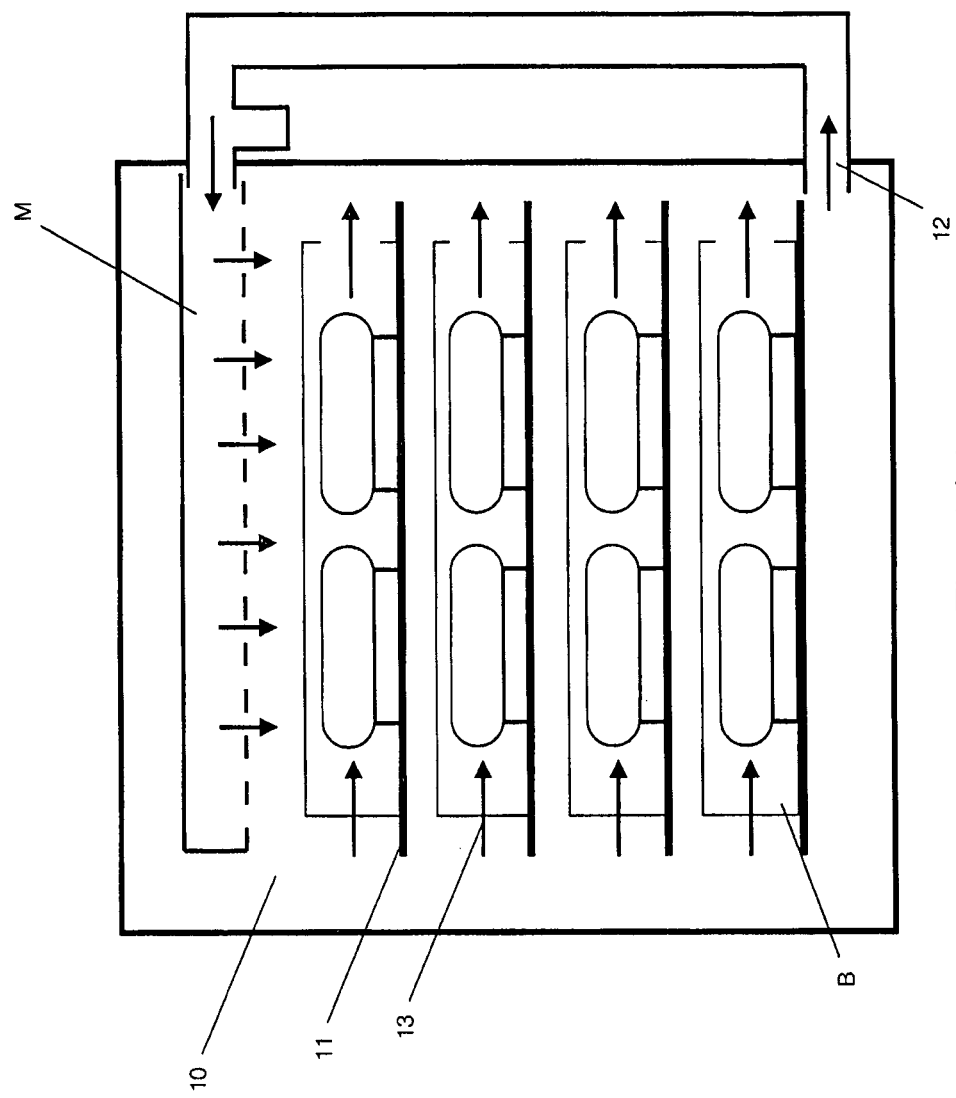
Fig. 3A1

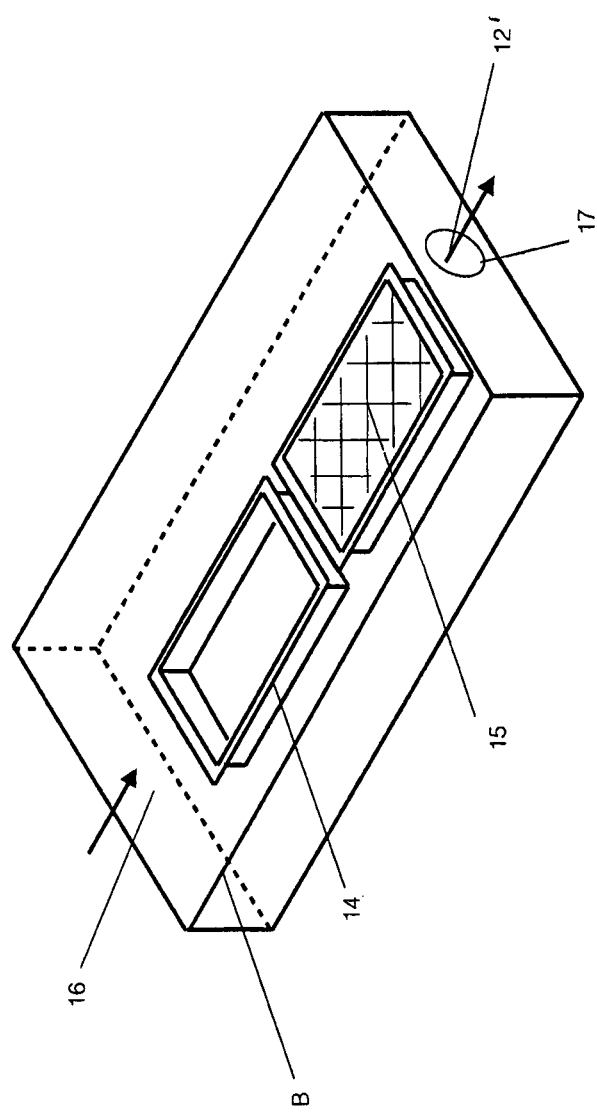
Fig. 3A2

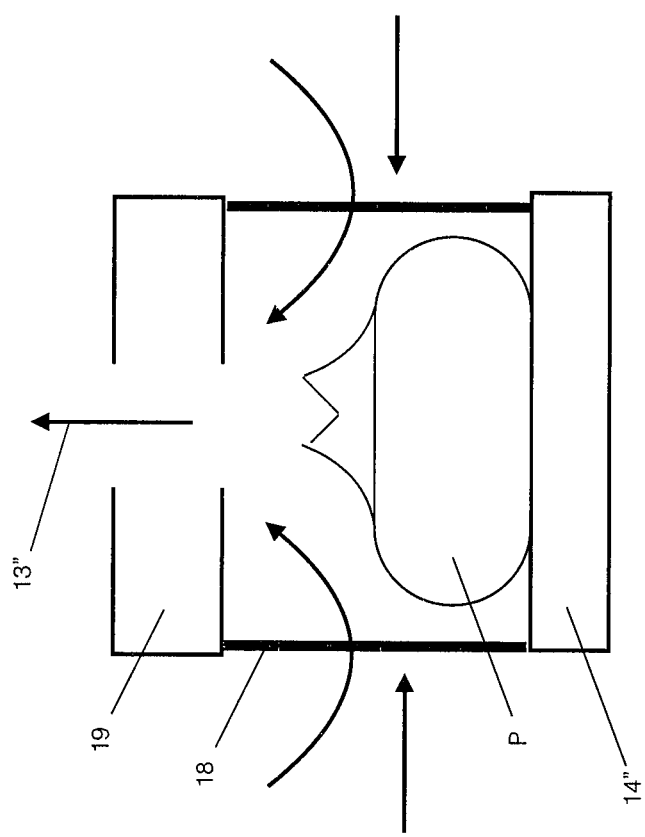

INCREASED HOMOGENEITY OF MYCOLOGICAL BIOPOLYMER GROWN INTO VOID SPACE

This is a Non-Provisional patent Application and claims the benefit of Provisional Patent Application 62/707,704, filed Nov. 14, 2017.

This invention relates to methods to create a biomaterial of increased homogeneity, strength and density as compared to the mycological biopolymer described in published US Patent Application US 2015/0033620 (A).

As described in published US Patent Application US 2015/0033620 (A), the environmental conditions for producing the mycological biopolymer product, i.e. a high carbon dioxide ($CO_2$) content (from 5% to 7% by volume) and an elevated temperature (from 85° F. to 95° F.), prevent full differentiation of the fungus into a mushroom. There are no stipe, cap, or spores produced. The elevated temperature accelerates tissue production. The biopolymer product grows into the void space of the tool, filling the space with an undifferentiated mycelium chitin-polymer, which is subsequently extracted from the substrate and dried.

Briefly, the invention allows for the production of a tough, pliable material that could be used to replace leather, leather-like materials, textiles and high density and strength foams in many applications such as upholstery, apparel/fashion, military gear, athletic gear, and footwear.

The invention involves growing a mycological biopolymer under conditions of directed airflow, depositing moisture and solutes, such as minerals, on the surface of the growing organism, growth through a scrim or lofted non-substrate matrix, and fluctuation of the humidity profile throughout growth to induce more homogenous material and produce a range of material densities. The mycological biopolymer product consists entirely of fungal mycelium.

One embodiment of the invention is the placement of contained inoculated growth media used to produce mycological biopolymer within a growth enclosure equipped to deliver a directed airflow across at least one of the surfaces of the growth media.

In this embodiment, the method of growing a biopolymer material comprises the steps of providing a plurality of containers, each of which defines a cavity containing a growth media comprised of nutritive substrate and a fungus; placing the containers in a closed incubation chamber; maintaining the incubation chamber with a predetermined environment of humidity, temperature, carbon dioxide and oxygen sufficient to produce a mycelium biopolymer while preventing full differentiation of said fungus into a mushroom; directing flows of air containing a high carbon dioxide content through the incubation chamber for passage over the growth media in each container; and incubating the growth media in each container for a period of time sufficient for the fungus to digest the nutritive substrate and produce a mycelium biopolymer consisting entirely of fungal mycelium in each container.

Each container may be placed within the incubation chamber within an "airflow box" such that the height of the container interacts with the airflow or each container may be sunk into the airflow box such that the total cross-sectional area of the box can be employed.

In accordance with the invention, the flows of air are directed into the closed incubation chamber laterally of the containers or perpendicularly of the containers.

A second embodiment of the invention employs the controlled deposition of moisture and minerals on at least one of the growing surfaces to induce homogeneity with a range of densities based on the moisture and mineral deposition volume.

In this embodiment, the method of growing a biopolymer material comprises the steps of providing a plurality of containers, each of which defines a cavity containing a growth media comprised of nutritive substrate and a fungus; placing the plurality of containers in a closed incubation chamber; maintaining the incubation chamber with a predetermined environment of humidity, temperature, carbon dioxide and oxygen sufficient to produce a mycelium biopolymer while preventing full differentiation of said fungus into a mushroom; distributing a mist through the incubation chamber for passage over the growth media in each container; and incubating the growth media in each container for a period of time sufficient to produce a mycelium biopolymer in each container.

In accordance with the invention, the mist includes moisture and a solute, such as minerals.

A third embodiment of the invention involves the growth of a mycological biopolymer through a scrim or lofted non-substrate matrix that is in direct contact or elevated above the substrate growth surface and grown in a container without the use of a lid.

A fourth embodiment employs the fluctuation of the percent humidity at time periods of growth throughout the duration of the cycle in order to induce a higher density material of increased homogeneity.

A fifth embodiment uses specific air flow rates to achieve a range of aerial mycelium densities and mechanical performances.

In all the embodiments of the invention, the mycological biopolymer is grown from a nutritious substrate, and grows into a panel at a dry density of 0.5 to 4 pounds per cubic foot. The localized environmental conditions, i.e. high carbon dioxide air, moisture deposition and temperature, must be homogenous, except for the embodiment using a scrim or lofted non-substrate matrix, in order to achieve uniform growth within each panel and throughout the larger growing chamber.

As further described in published US Patent Application US 2015/0033620 (A) the use of a lid was enlisted to control the localized environmental conditions influencing the growth of the mycological biopolymer.

In accordance with the invention, under directed airflow, the lid on the container is removed and the localized environmental conditions are homogenized via airflow. The use of airflow allows for growth from the full surface of the growth container and helps to improve the homogeneity and uniformity of the tissue grown. This may be attributed to the airflow facilitating the delivery of humidity, water and solutes, such as minerals, to the growing tissue, elimination of microenvironments, and/or increased mechanical force. There are many applications for a biological textile and foam that require increased volume of homogenous material.

The growth environments used in the production of edible mushrooms, both specialty and *Agaricus* currently employ the use of some uncontrolled airflow through the growth chambers for heating, cooling, of gassing carbon dioxide produced by the growing mushrooms or introducing oxygen into the growing chamber. This differs from the airflow technology employed to prevent any and all differentiation of the fungus into a fruiting body that makes an edible mushroom while providing a uniform environment to grow mycological biopolymer Further, airflow within the cultivation of mushrooms is directed at removing metabolic byproducts such as carbon dioxide and other volatiles, and is intermittent in nature. The airflow employed to grow mycological biopolymer is directed at providing a consistent homogenization of the incubation environment without localized variations that has sufficiently controlled parameters (e.g., high carbon dioxide) such that the mycelium cannot differentiate into a mushroom. Also, the airflow velocity provides a directed force that modulates the structure of the aerial mycelium, impacting density.

While the growth environments used in the production of edible mushrooms can employ the use of an airflow through the growth chambers, the air flow is indirect and part of a recirculating system for humidification of the environment. The airflow is not directed across the surface of the growth media as is the case in accordance with the invention.

These and other objects and advantages will become more apparent from the following detailed description taken with the accompanying drawings wherein.

Figure 2:
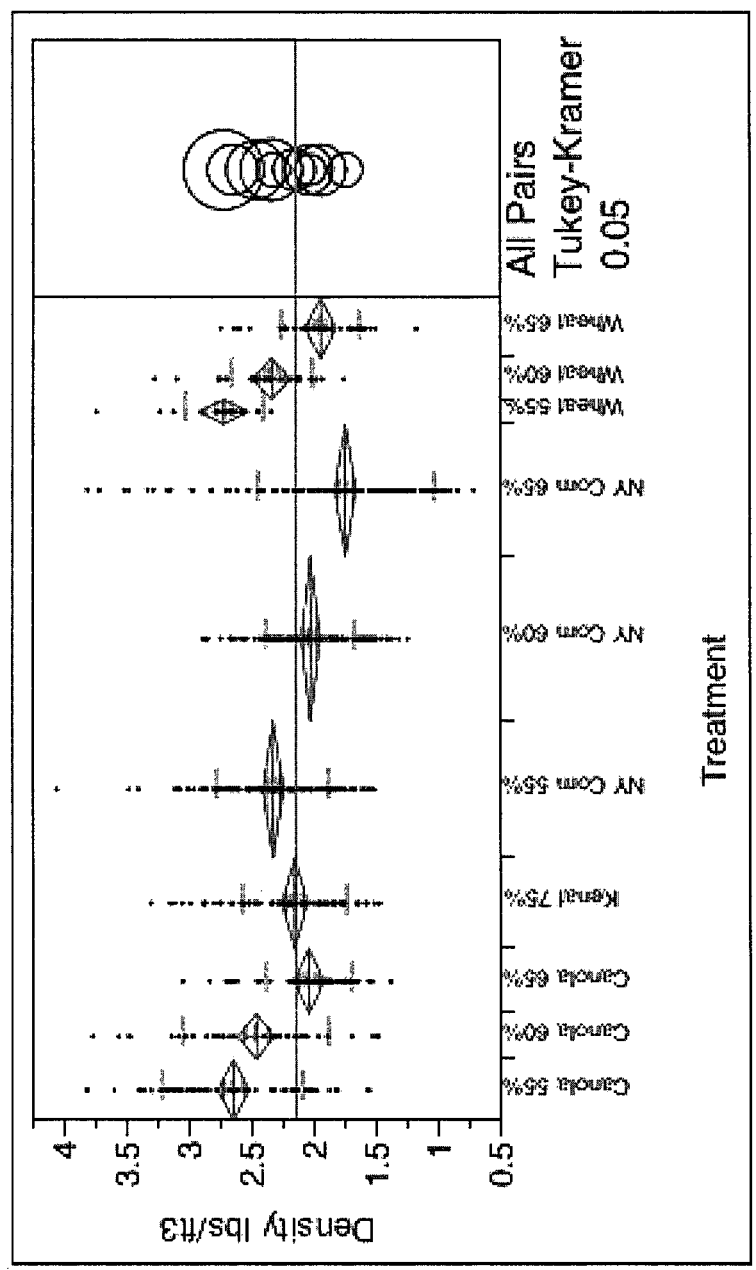
FIG. 2 illustrates a chart of treatment versus density in accordance with the invention.
Figure 3B:
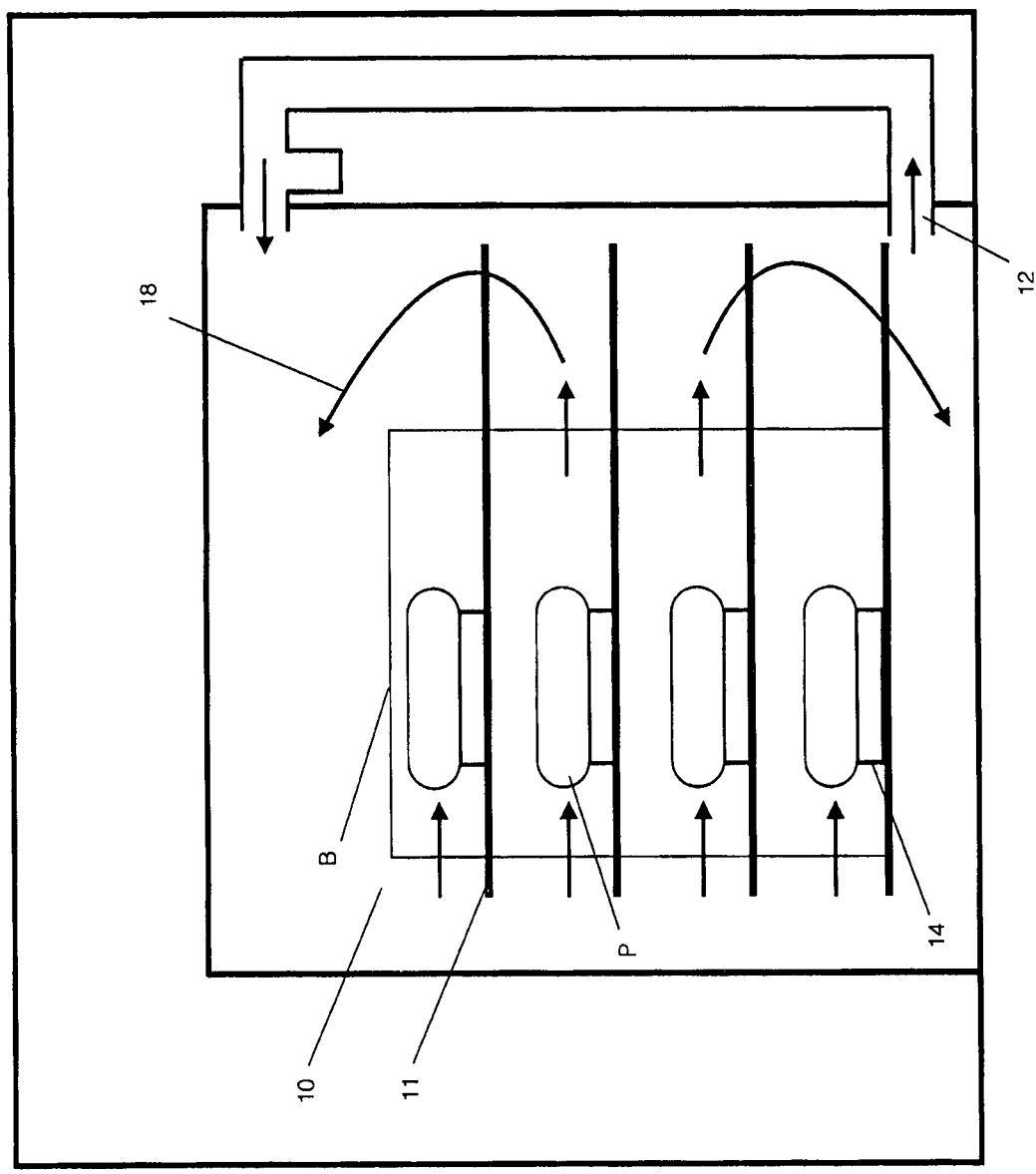
Figure 3C:
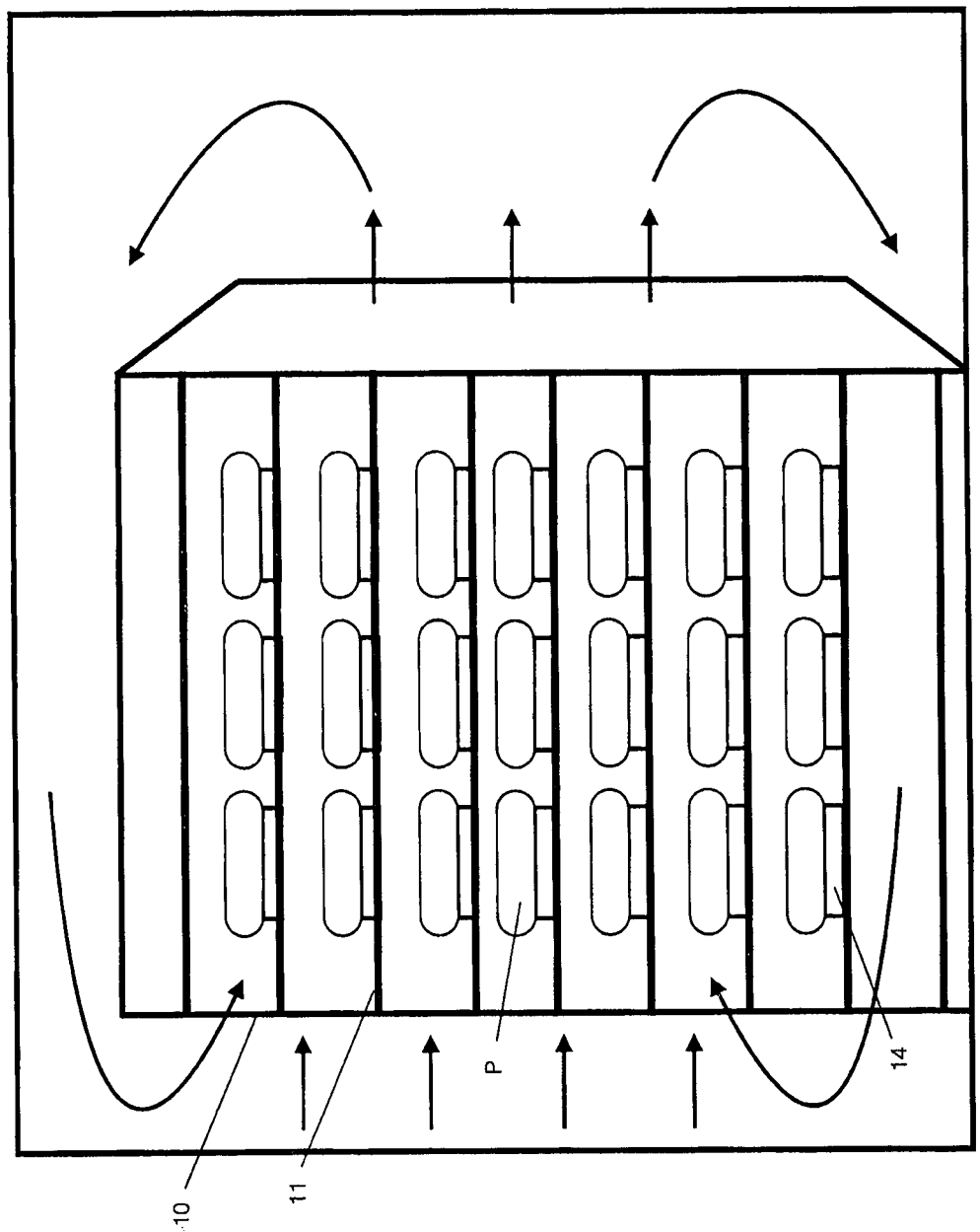
Figure 4A:
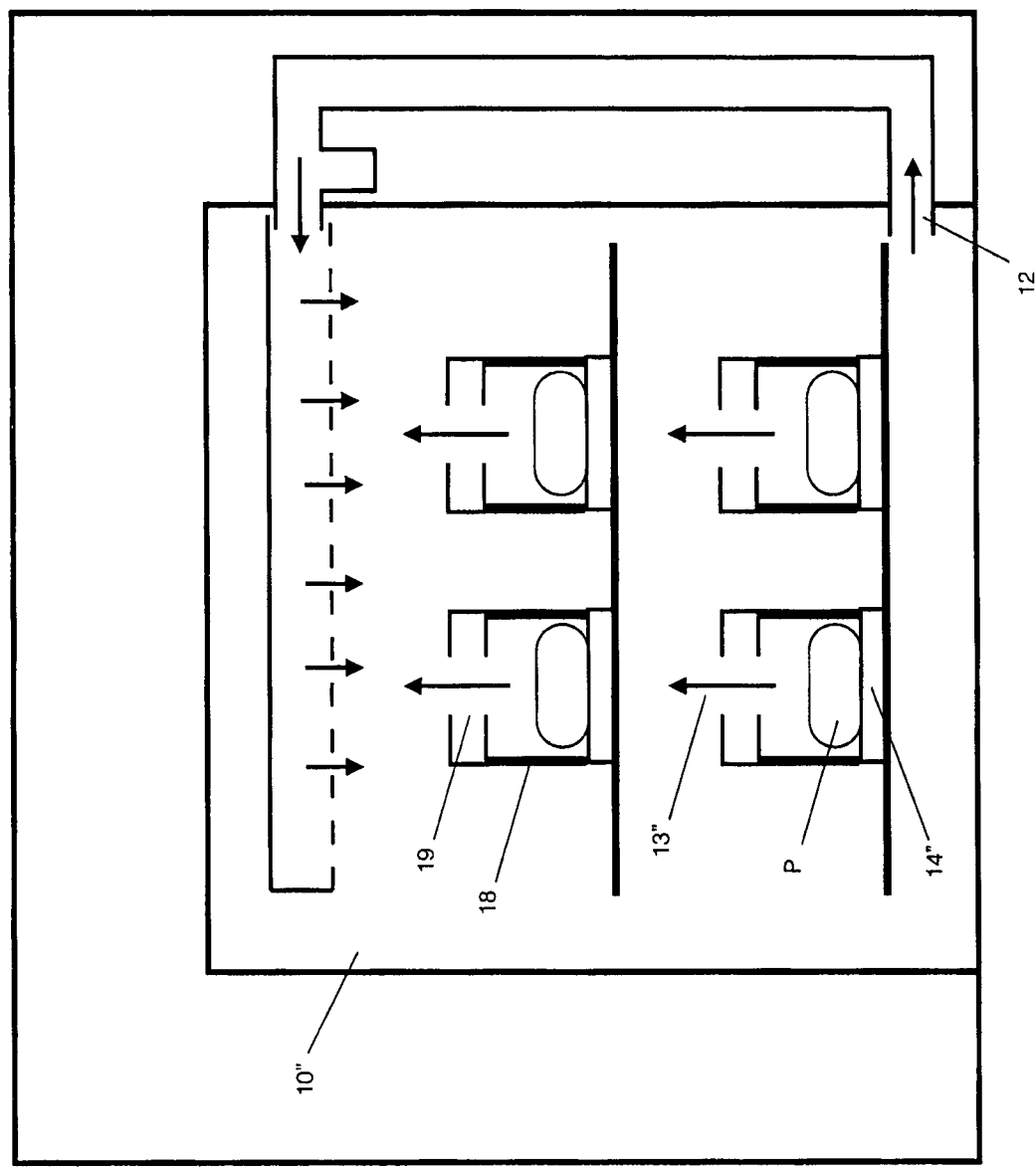
Figure 4B:
Figure 5A:
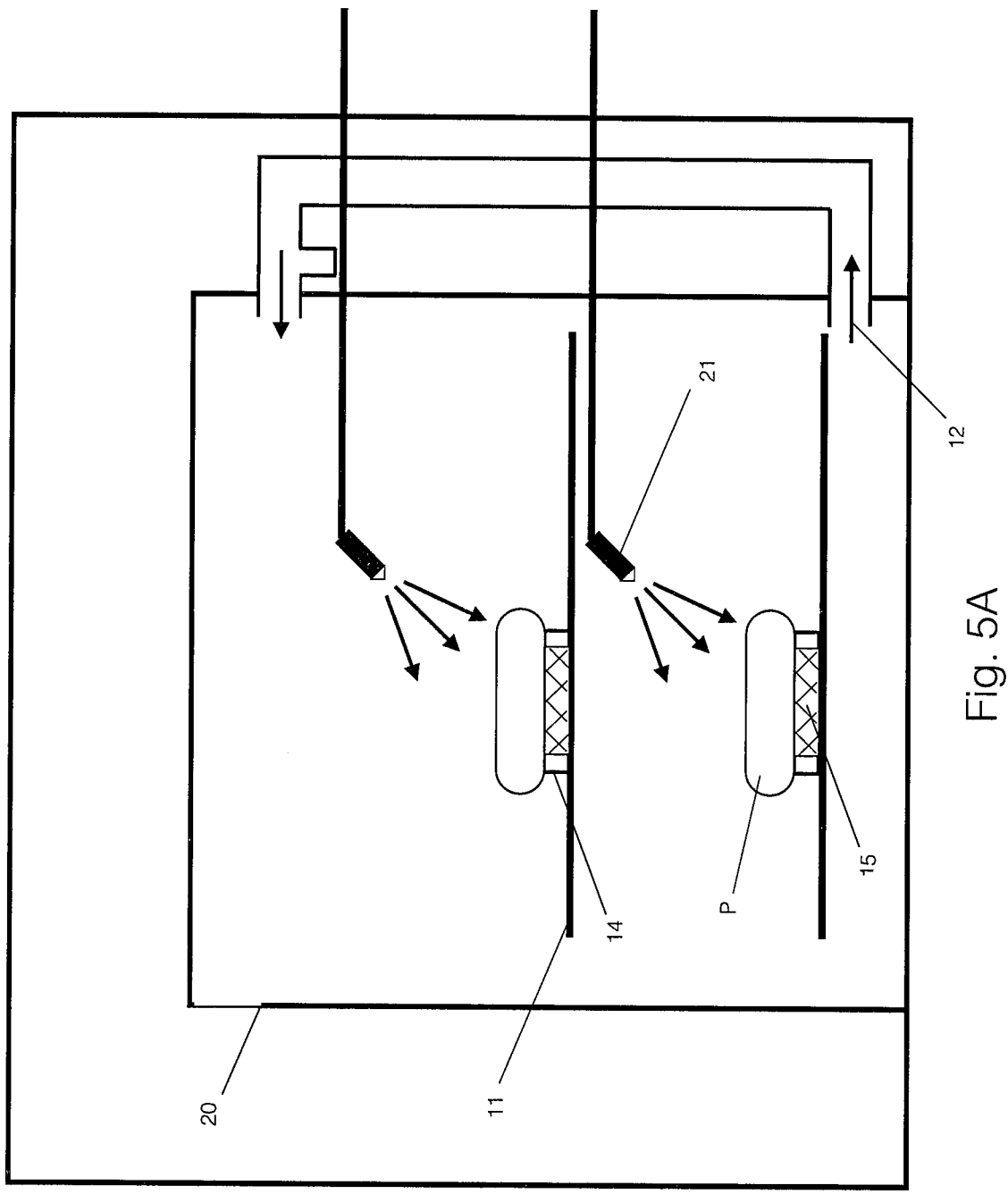
Figure 5B:
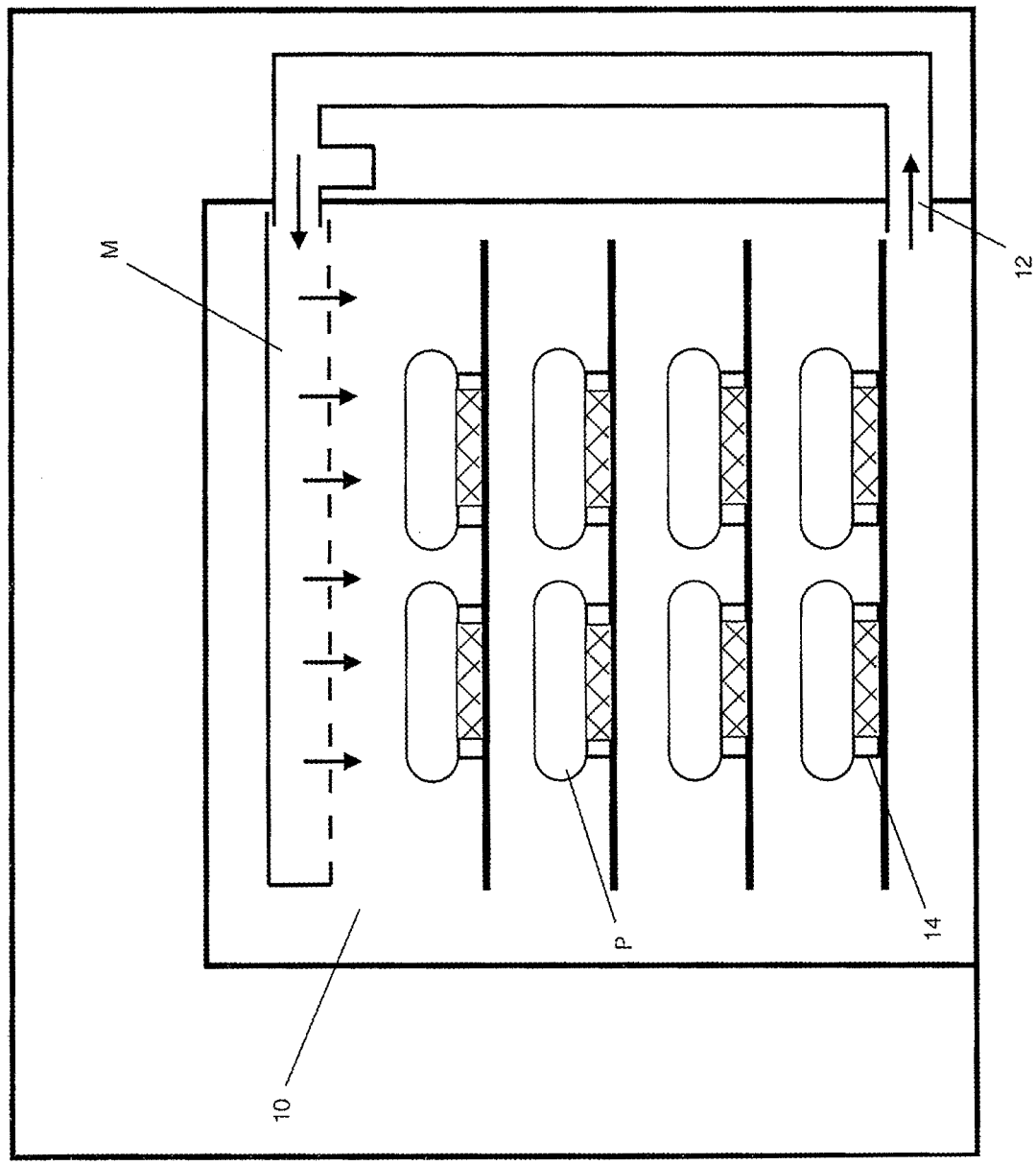

FIG. 3A1 schematically illustrates a lateral airflow system in accordance with the invention;

FIG. 3A2 illustrates a perspective view of an air box used for the incubation of two containers in accordance with the invention FIG. 3B schematically illustrates a modified lateral airflow system in accordance with the invention;

FIG. 3C schematically illustrates another modified lateral airflow system in accordance with the invention;

FIG. 4A schematically illustrates a perpendicular airflow system for passing air over the surface of the growth medium in accordance with the invention;

FIG. 4B illustrates a photograph of the top surface of a panel grown in the system of FIG. 4A;

FIG. 4C schematically illustrates the air flow patterns over a growth medium in the system of FIG. 4A;

FIG. 5A schematically illustrates a mist distribution system in accordance with the invention; and FIG. 5B schematically illustrates an indirect air flow system for recirculation of humidified air not in accordance with the invention.

Referring to FIG. 3A1, in a first embodiment, the method of growing a biopolymer material employs a closed incubation chamber 10 having a plurality of vertically spaced apart shelves 11 and transparent front walls (not shown) for viewing the interior of the chamber 10.

In addition, an air flow system 12 is connected with the chamber 10 for directing air flows laterally across the chamber 10 as indicated by the arrows 13 from one side of the chamber 10 to and through the opposite side of the chamber 10. As illustrated, the air flow system 12 includes a manifold M in the upper part of the chamber 10 for distributing humidified air across the top of the chamber 10 for cascading down the shelves 11 until being recirculated on the bottom right for re-humidification.

Each shelf 11 of the chamber 10 is sized to receive an air box B that contains two containers 14 each of which contains a growth media 15 comprised of nutritive substrate and a fungus.

Referring to FIG. 3A2, each container 14 is in the form of a rectangular tray with an open top to define a cavity of a size of 11.5 inches by 18.5 inches with a 1 inch lip around the entire container that extends externally outwardly of the cavity. Each container is placed within the air box B.

The containers 14 are constructed from a sufficiently rigid, non-reactive material, such as polycarbonate, and the orifice of the container is such that it is paired with the airflow device to achieve the desired air flow rates. The length of the container along with the airflow rates dictate the consistency of this flow, and the entrance length before the airflow reaches the growing part is impart to control the laminar or turbid nature of the flow. The containers can include ramps, fairings, such as airfoils, or baffles, to assist in homogenizing the flow.

The air box B is of rectangular shape that receives the growth trays 14 and has an open side 16 in one end face and a smaller orifice 17 in an opposite end face.

The air flow system 12 includes a fan 12' situated at the orifice 17 of each air box B to pull air over the growth media 15 in the containers 14 and growing part as indicated by the horizontal arrows. The orifice is covered by the fan to ensure all of the air moves through the fan. Alternatively, the fan 12' may be positioned at the open side 16 of the air box B to push air over the growth media 15.

As indicated, the humidified air cascading down from the manifold M passes into and through each air box B via the orifices 16, 17.

Specifically, the growth media 15 comprises:

| Materials Input | Approximate Materials Amount |
|---|---|
| Bagged Sealed Substrate: | |
| Corn stover | 6000 g |
| Poppy Seeds | 1440 g |
| Maltodextrin | 256 g |
| Calcium sulfate | 80 g |
| Municipal water | 16000 g |
| Inoculant: | |
| Ecovative Strain ID 045-08-003 spawn | 2880 g |

During the method of growing a biopolymer material, the incubation chamber 10 is maintained with a predetermined environment of humidity, temperature, carbon dioxide and oxygen. Specifically, the chamber 10 is maintained at 99% relative humidity (RH), 5% $CO_2$, and a fluctuating temperature of from 85° F. to 90° F. during the step of incubating.

The incubation chamber 10, i.e. growth enclosure, can be open on one end and on the other can be outfitted with fans or apparatuses for moving air over the containers 14 in a lateral direction as indicated by the arrows 13 either by pulling or pushing air at speeds ranging from 5 CFM to 10,000 CFM steadily or in a pulsing fashion. The incubation chamber 10 can be within a larger incubation chamber (not shown) that is able to maintain environmental conditions including humidity, temperature, carbon dioxide and oxygen.

The shape and construction of the incubation chamber 10 can be specially crafted to assist in directing the air flow and laminar or turbid characteristics of the air flow.

Process Steps (see FIG. 3A1)
Directed Lateral Airflow
1. Nutritious growth media and organism inoculum 15 is packed into containers 14 as described in US 20150033620 A with the exception that these containers 14 are not outfitted with lids.
2. These containers 14 are placed within air boxes B on the shelves 11 of the enclosed incubation chamber 10.
3. Directing flows of air via the airflow system 12 through the incubation chamber 10 for passage laterally over the growth media 15 in each container 14 as indicated by the arrows 13.
4. incubating the growth media 15 in each container 14 for a period of time sufficient to produce a panel P of mycelium biopolymer in each container 14, e.g. panels can be grown for 4 to 14 days within the incubation chamber 10.

The flows of air are generated by fans outfitted to the incubation chamber 10 and are directed over the containers 14 and back into the greater incubation space.

Figure 1A:
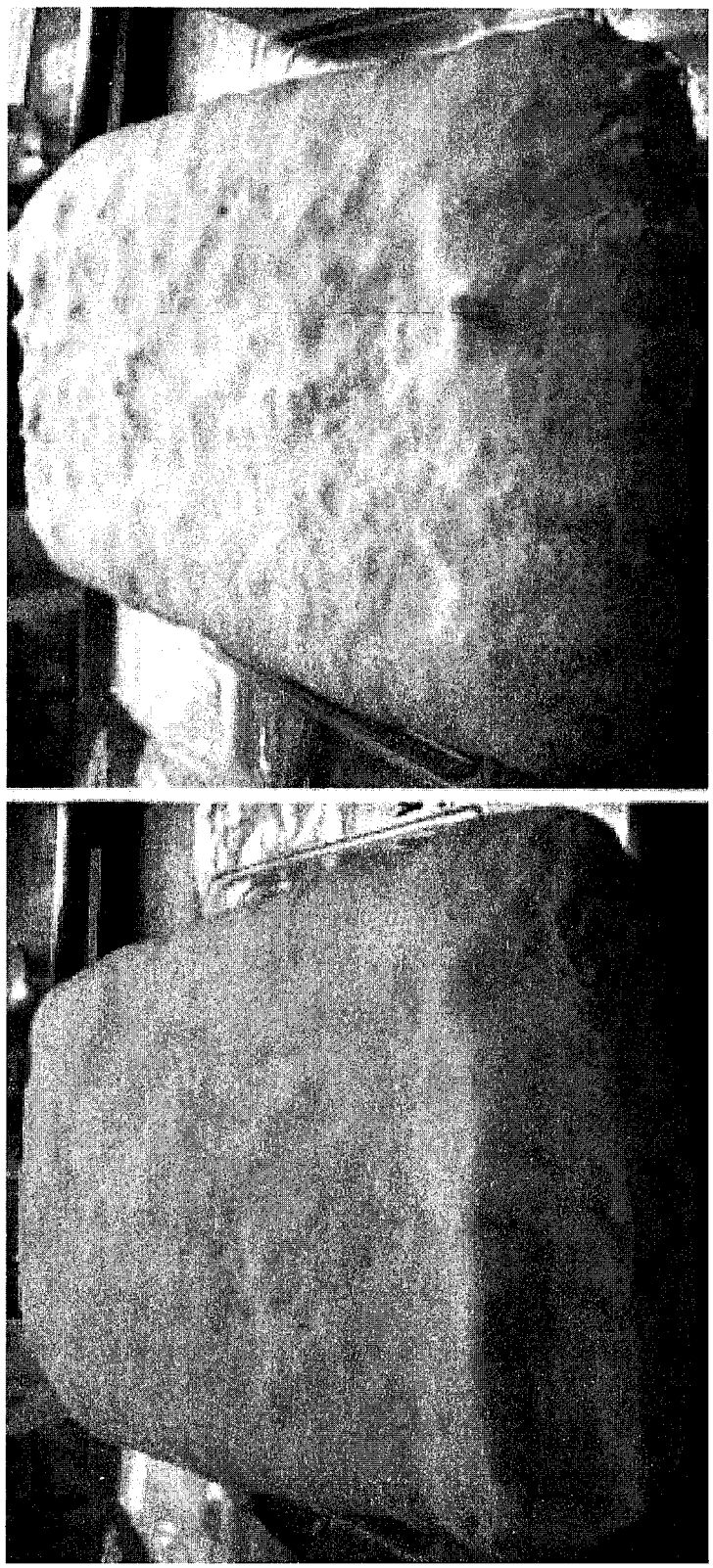
FIG. 1A illustrates photographs of the top surfaces of panels grown in a direct, high airflow environment with minimal differentiation in tissue morphology in accordance with the invention.

Referring to FIG. 1A, a pair of panels 17 produced in accordance with the above method consists entirely of fungal mycelium and show minimal differentiation in tissue morphology.

Airflow rates of 100 cubic feet per minute at a constant RH of >99% resulted in tissue with a dry density of 1.98 pcf and a tensile strength of 17.5 psi. These panels offered a high degree of consistency.

Airflow rates of 100-175 cubic feet per minute and relative humidity drop to 96% for a period of 48 hours resulted in tissue with a dry density of 1.45 pcf and a tensile strength of 13.6 psi. These grown panels resulted in a high degree of consistency.

Airflow speeds of 300-350 cubic feet per minute and at a constant RH of >99% resulted in tissue with a dry density of 3.32 pcf and a tensile strength of 31.2 psi.

Figure 1B:
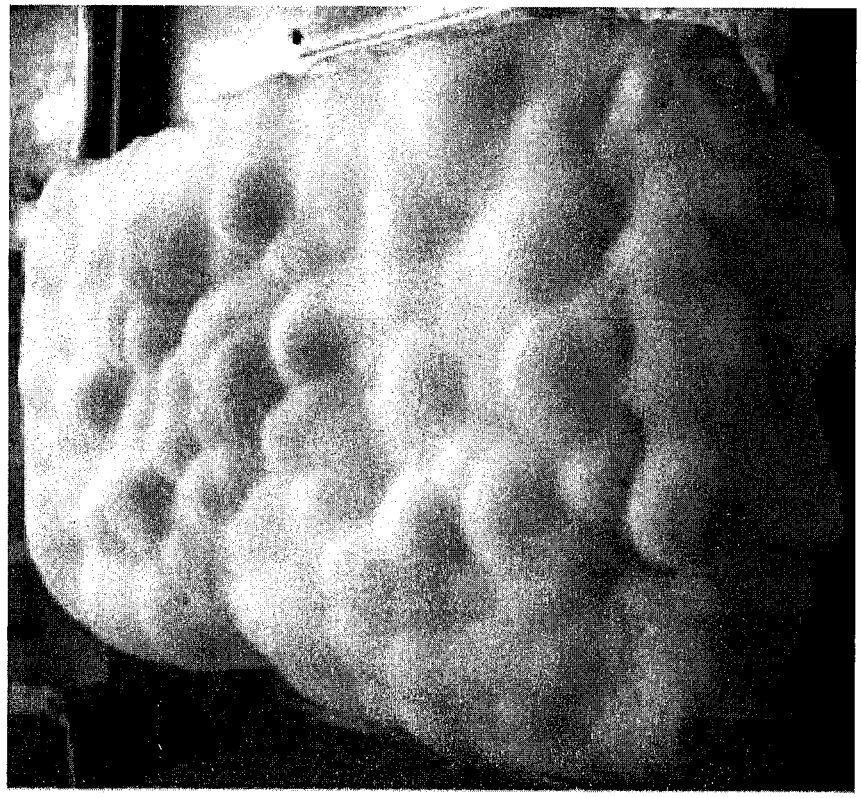
FIG. 1B illustrates photographs of the top surfaces of panels grown in an indirect, low airflow environment with highly differentiated tissue.
Figure 1B:
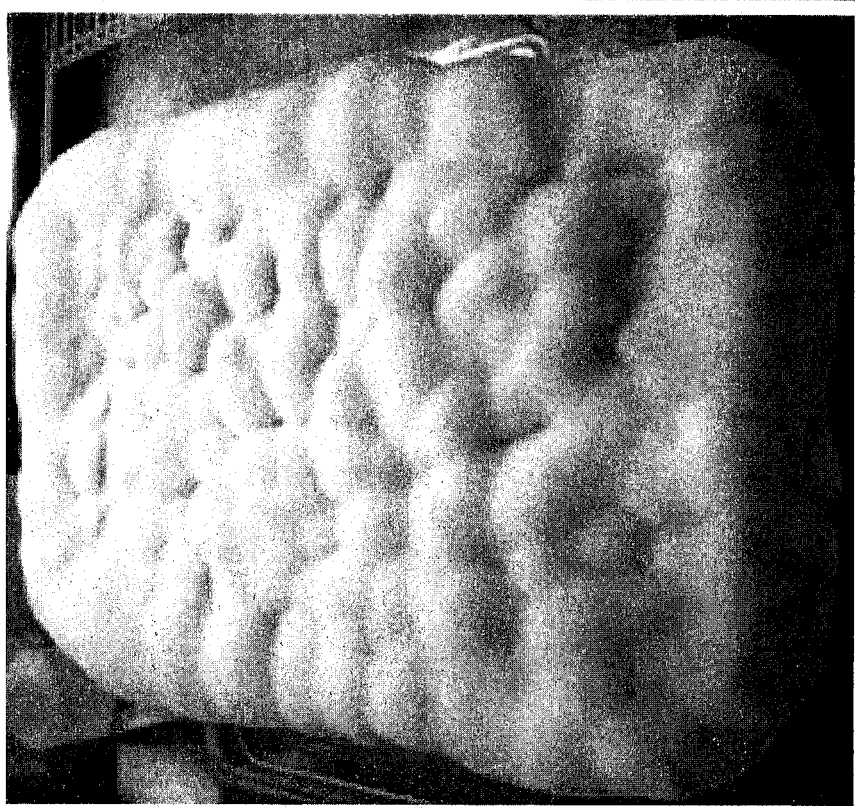

Referring to FIG. 1B, pairs of panels produced under conditions without a directed airflow were characterized in having highly differentiated tissue.

Figure 1C:
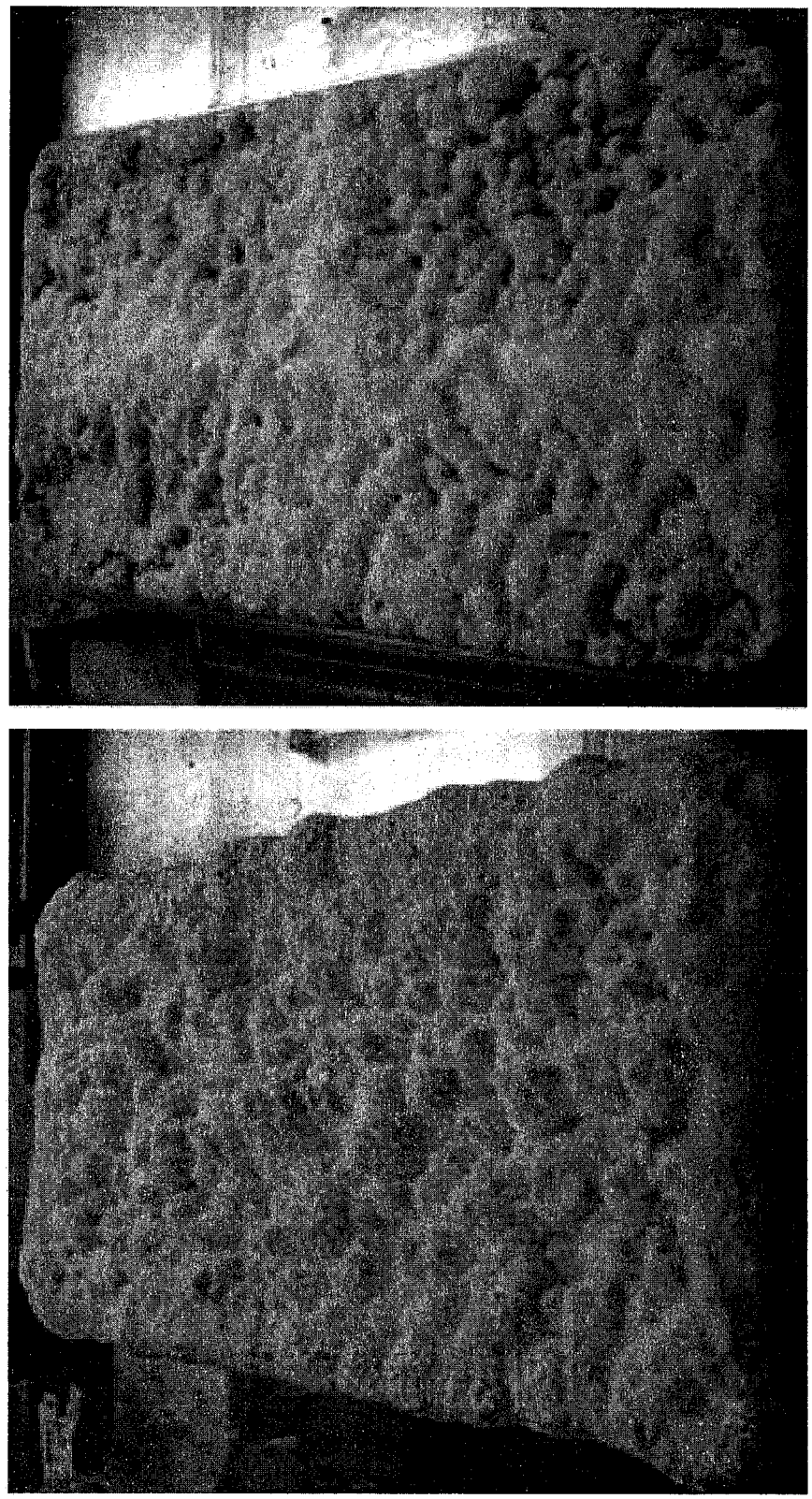
FIG. 1C illustrates photographs of the top surfaces of panels grown in a zero-airflow environment and resulting in highly differentiated tissue and reduced aerial growth.

Referring to FIG. 1C, pairs of panels grown in a zero-airflow environment were characterized in having highly differentiated tissue and reduced aerial growth;

Referring to FIG. 3B, wherein like reference characters indicate like parts as above, the incubation chamber 10 may be constructed with vertically spaced apart shelves 11 (or racks) and may be enclosed by sheeting (not shown) for cooperation with containers 14 of extended length such that each shelf 11 receives an air box B with only a single container 14.

In addition, the incubation chamber 10 is outfitted with a lateral airflow system 12' having fans fitted to the chamber 10' to direct airflow from the incubation environment through the air boxes B and over the containers 14 and back into the greater incubation space as indicated by the arrows 18.

Referring to FIG. 3C, wherein like reference characters indicate like parts as above, the incubation chamber 10' may have open shelves 11 on which containers 14 with growth medium 15 are placed without using air boxes. In addition, the incubation chamber 10' is outfitted with a lateral airflow system having fans (not shown) located on the right-hand side, as viewed, of the chamber 10' for pulling air flows through and out of the chamber 10' while passing laterally over the containers 14.

Referring to FIG. 4A, wherein like reference characters indicate like parts as above, the growth of the mycological biopolymer may be effected by passing the airflows perpendicularly of the containers 14.

For example, the enclosed incubation chamber 10" may be constructed with one or more air flow devices (not shown) positioned above the nutritive media 15 to push or pull conditioned air over the growing mycelium. The air flow device 12 as in FIG. 3A1 is either held static at a desired height above the growth container 14' or modulated on linear actuators (not shown) through the course of growth.

As illustrated, two containers 14' are positioned on each shelf 11 within the incubation chamber 10" and each container 14' is provided with vertical standoffs 18 that space a cover 19 (roof) from a container 14'. The vertical standoffs 18 are fabricated from a non-reactive substance, such as polyvinylchloride (PVC), and are sufficiently rigid to resist the forces of the airflow device.

The incubation chamber 10", can be open on one end and on the other can be outfitted with fans or apparatuses for moving air over the containers 14' in a direction perpendicular to the growing surface as indicated by the arrows 13" either by pulling or pushing air at speeds ranging from 5 CFM to 10,000 CFM steadily or in a pulsing fashion.

The incubation chamber 10" can be within a larger incubation chamber (not shown) that is able to maintain environmental conditions including humidity, temperature, carbon dioxide and oxygen.

Referring to FIG. 4B, a panel of mycological biopolymer produced in the incubation chamber 10" may be characterized in having a concentration of mycelium below the airflow device as the air was pulled up over the growing surface as indicated in FIG. 4C as opposed to across the growing part in FIG. 1A. As indicated in FIG. 4B, where airflow device pulled the air upwardly from a central region of the growth medium, the growing mycelium was concentrated in the central region of the panel.

Directed Perpendicular Airflow (See FIG. 4A)
1. Nutritious growth media and organism inoculum is packed into containers as described in US 20150033620 A with the exception that these containers are not outfitted with lids.
2. These containers 14" are placed within the enclosed incubation chamber 10".
3. Directing flows of air via the airflow system 12 through the incubation chamber 10" for passage perpendicularly of the growth media in each container 14" as indicated by the arrows 13".
4. The shape and design of the growth enclosure can be specially crafted to assist in directing the flow and laminar or turbid characteristics of the air.
5. incubating the growth media 15 in each container 14" for a period of time sufficient to produce a panel of mycelium biopolymer in each container 14", e.g. panels can be grown for 4 to 14 days within the incubation chamber 10".
6. Air movement can be used to mold and structure the material into particular shapes and patterns during growth for a final product that is shaped using airflow.

In Step 6 above, pulled horizontal airflow velocity (>175 cfm) creates a dense scalloped pattern. Vertical airflow creates structures below the airflow device presenting a morphology that parities the airflow (pulled upward like a stalagmite). Pushing creates wave patterns opposing the airflow (160 CFM). Proximity to the airflow device and the pattern of airflow generates tissue patterns that mimic the flow.

Referring to FIG. 2, as graphically illustrated, the moisture and solute content of the growth media has been found to directly relate to the density of the material being grown. The higher the moisture content, the lower the density of the material grown, a trend that has been shown across an assortment of substrate types.

FIG. 2 shows three other substrate varieties in comparison to the corn stover material at 4 different moisture contents. This resulted in variations in the final product density, which higher moisture contents resulting in lower density tissue.

Tukey Kramer is a mean (average) comparison test that determines the significant difference between tests. The 0.05 is the confidence interval, so there is a 95% confidence in the relationship between the data.

The ability for fungal cells to fill the void space is dependent on the water and solutes available to the organism during growth. The more water available, the more aggressively the organism can expand, causing the density of the material to drop.

Accordingly, referring to FIG. 5A, wherein like reference characters indicate like parts as above, an enclosed incubation chamber 20 is fitted with a mist distribution system 21 so that moisture and solutes can be applied to the growing tissue through a number of avenues for the purpose of producing a range of material densities in the produced mycological biopolymer.

As illustrated, the incubation chamber 20 has a plurality of vertically spaced apart shelves 21 and transparent front walls (not shown) for viewing the interior of the chamber 20. The incubation chamber 20 is sized to receive a plurality of containers 14, each filled with a growth media 15.

As above, the incubation chamber 20 can be placed within larger incubation chambers that are able to maintain uniform environmental conditions including humidity, temperature, carbon dioxide and oxygen.

The mist distribution system 21 is positioned to deliver moisture and solutes, such as minerals, to the top of the growing tissue in each container 14 and can also be used to control the material density and regulate the homogeneity of the material. This material is comprised of aerial hypha growing up and out of a nutritious space into a non-nutrient environment. In order to control growth in such an environment, the organism employs the use of turgor pressure to regulate the extension of the hyphae at the apex, or hyphal tip. Thus, regulating the amount, distribution and/or droplet size of available moisture and solutes deposited across the top surface of the growing material can control the osmotic gradient created within the hyphae and subsequently, its growth rate and pattern of colonization.

Solutes are any agent that can cause an osmotic potential. RO (reverse osmosis) or distilled water are free of such agents. Other solutes could include proteins, carbohydrates, polymers, and minerals.

A solute is a material that induces an osmotic potential within a solution. A solute can be a mineral, a carbohydrate, a protein, or lipid. Concentrations of a solute on one side of a membrane, such as a cell membrane and/or wall, will drive a potential across the membrane if the solution on the opposing side of the membrane has a lesser concentration of the solute.

Moisture and solute deposition can be employed to achieve specific material densities and increase material homogeneity.

Moisture and solutes can be distributed across the growing surface of the growth media using a bath of water outfitted with a "humidifying puck" that atomizes the water into vapor or mist. A "humidifying puck" is an ultrasonic humidifier which produces low quality, high liquid content, droplets of a size range of 5 to 22 microns. The liquid water droplet, opposed to vapor, is important as the droplet can carry a solute. The same is true for sprays or bubblers, but cannot be achieved with steam. Steam can be used to regulate humidity, but not as a substitute for water carrying the solutes.

This mist can be distributed across the surface of the growth media using indirect airflow from a fan or similar apparatus or by a spray nozzle that can be outfitted with compressed air or other means of expelling the moisture out of the nozzle and directed at the growing surface of the growth media.

The amount of moisture and minerals, the distribution, and the droplet size can be regulated to produce a homogenous mycelium biopolymer of varying densities.

Fluctuation of the percent humidity during the growth cycle can be employed as a method to increase the density and homogeneity of the material. In the method described in the published US 2015/0033620 A, the humidity was held static throughout the duration of the growth cycle to achieve material growth. By altering this paradigm and fluctuating the humidity of the growth chamber at targeted stages during the growth cycle, the density and homogeneity can be increased.

A moist environment is generally necessary for fungi to grow aggressively. When a desiccating environment is encountered, many species of fungi have developed methods to protect themselves against moisture loss. For aerial hyphae, a localized high humidity environment is necessary to allow for continued expansion and prevent collapse of the hyphae towards the growing surface. Fluctuation of the humidity in the growth chamber can be used to trigger physiological responses of the organism to a desiccating environment as well as to manipulate the aerial hyphal growth in order to achieve the desired material characteristics.

A system design allowing for the controlled deposition of mist onto the growing material without the use of airflow was prototyped and tested employing the incubation chamber of FIG. 5A. This misting system prototype evenly distributed an equivalent volume of mist onto the growing material as a control high airflow system. The misting system used a SF1010SS siphon fed atomizing nozzle, or "atomizer" to expel a fan shaped spray of fine water droplets, equivalent in size to MycoFlex™ control technology as employed in the methods described in US 2015/0033620, across the growing surface of the experimental parts without the use of direct airflow.

The atomizer misting system was set up with the nozzle positioned 26.5 inches in from the incubator wall to the right side of the target growth surface. The nozzle was affixed at a 45-degree angle to the shelf 11 above the target container 14 and rotated 90-degrees, resulting in a vertically oriented fan-shaped spray pattern. The target total volume of moisture of 0.28 microsiemens per centimeter (uS/cm) per minute plus/minus seven microsiemens per centimeter (uS/cm) as well as target deviation in moisture across the panel surface of 0.00014 g/min was achieved using a misting paradigm of 2.4% time misting over a 1 minute period. The target volume was based on TDS values collected for the direct, high airflow incubations system of FIG. 3A1.

This atomizer misting system was trialed with biomass to assess the impact of moisture deposition independent from airflow. Seven parts were loaded into a lab incubator equipped with the atomizer misting system without any airflow (FIG. 5A).

Humidification of this system was achieved by the moisture input into the system via the atomizer.

Two control incubators were run simultaneously using the standard biopolymer humidification system and environmental conditions. One control incubator was set up using the standard direct, high airflow box system and the humidification recirculation system (FIG. 3A1) while the other was equipped with only the low, indirect airflow used for the recirculation of humidified air (FIG. 5B). All three incubators were set to standard biopolymer environmental conditions of 99% RH, 5% CO2 and fluctuating temperature of 85-90 degrees Fahrenheit for nine days of growth.

Direct, high airflow resulted in increased homogeneity of growth within the panels across the entire incubator and allowed the production of the panels of FIG. 1A with minimal differentiation in tissue morphology.

The zero-airflow incubator equipped with the atomizer misting system resulted in highly differentiated panels with a low volume of vertical growth (FIG. 1C). A panel grown by this technique may be characterized in having "bulbs" or bundles of mycelium fibers from 0.1 to 1 inch in diameter and in having discrete dense regions predominantly void of connective tissue.

The low, indirect airflow incubator also resulted in highly differentiated material and reduced aerial growth; however, the volume of vertical growth was increased (FIG. 1B). A panel grown by this technique may be characterized in having "bulbs" or bundles of mycelium fibers equal to or greater than 0.6 inches, for example of from 0.6 to 4 inches in diameter. By comparison, the "bulbs" of mycelium fibers on the panel of FIG. 1C are less than 0.6 inches.

Further, the panel of FIG. 1B is characterized in that the connective tissue is minor and results in a homogeneous aesthetic but heterogeneous performance. This means that, although the surface looks smooth, the mechanical performance may vary through the section of the part.

The high, direct airflow growth environment resulted in panels that were significantly more homogenous, with minimal differentiation throughout the panels (FIG. 1A).

Process Steps

Moisture and Mineral Deposition on Material Surface During Growth

1. Nutritious growth media and organism inoculum was packed into containers 14 as described in US 20150033620 A with the exception that these containers 14 were not outfitted with lids.
2. These containers 14 were placed within the incubation chamber 10 maintained under predetermined environmental conditions including humidity, temperature, carbon dioxide and oxygen.
3. Moisture and minerals were distributed across the growing surface of the media in the containers using a bath of water outfitted with a humidifying puck that atomizes the water into vapor or mist.
4. Panels were grown for 4 to 14 days within the incubation chamber 10.

Regulation of Moisture and Minerals within the Substrate to Control Tissue Density Tests were conducted to determine the effect of regulating the moisture and minerals within a substrate (growth media) prior to incubation in an enclosed incubation chamber with respect to the density of a produced panel of mycological biopolymer.

One test used the following steps:
1. Nutritious growth media and organism inoculum was packed into containers 14 as described in US 20150033620 A with the exception that these containers 14 are not outfitted with lids.
2. Moisture and minerals were distributed within the growth media to achieve a specified moisture between 20-95% moisture.
3. Incubating the growth media 15 in each container 14 for a period of time sufficient to produce a panel of mycelium biopolymer in each container 14, panels were grown for 4 to 14 days within the incubation chamber 10.

The result of the test was that the amount of moisture and minerals within the growth media prior to placement in the incubation chamber can be regulated to produce a homogenous panel of mycological biopolymer of a desired density. Of note, moisture contents of 65% on corn stover substrate resulted in densities of 1.7 pcf, and moisture contents of 55% resulted in densities of 2.7 pcf.

In another embodiment, the mycological biopolymer may be grown through a scrim or lofted non-substrate matrix. In this embodiment, the scrim or lofted non-substrate matrix is either organic or inorganic in nature and offers sufficient porosity such that the mycelium can infiltrate the material. The scrim or lofted non-substrate matrix is positioned on or above the nutritive substrate and the entire assembly is incubated in one of the configurations above. The scrim or lofted material serves as reinforcement to the mycelium, a means of oriented and directing tissue growth, a method for consistently removing the grown tissue from the nutritive substrate, or a combination thereof.

In a fourth embodiment, the fluctuation of the percent humidity at time periods of growth throughout the duration of the cycle is employed in order to induce a higher density material of increased homogeneity. In this embodiment, the relative humidity is sustained at a high percentage during the period of aerial mycelium induction, which can begin between day 0 and 5 of growth. Once induced, the humidity is reduced to less than 98% for a period of 4 to 72 hours to induce a densification of the apical tissue. The humidity can then again be elevated to induce newly differentiated growth to provide a range of density, tissue morphology, and orientation through the cross-section of the product. This can be repeated as many times as necessary to garner desired variations in performance through the mycological foam.

In a fifth embodiment, specific air flow rates are used to achieve a range of aerial mycelium densities and mechanical performances. In this embodiment, the air flow can be set at a constant rate, such that the air flow velocity is passively modulated at the tissue grows, or the rate can be adjusted through the course of incubation to deliver a constant rate over the growing tissue. Higher airflow rates have demonstrated the production of denser tissues, while lower airflow rates result in a higher loft of tissue that is less dense when dried.

What is claimed is:

1. A method of growing a biopolymer material comprising the steps of:
   providing a plurality of containers, each said container defining a cavity containing a growth media comprising nutritive substrate and a fungus;
   placing said plurality of containers in a closed incubation chamber;
   maintaining said closed incubation chamber with a predetermined environment of humidity, temperature, carbon dioxide content and oxygen content sufficient to produce a mycelium biopolymer consisting essentially of fungal mycelium;
   directing flows of air containing said carbon dioxide content through said incubation chamber;
   incubating the growth media in each said container; and passing said flows of air over the growth media in each said container;

wherein the incubating is for a period of time sufficient for said fungus to digest said nutritive substrate and produce the mycelium biopolymer consisting essentially of fungal mycelium in each said container.

2. The method of claim 1 wherein said flows of air are directed into said closed incubation chamber laterally of said containers.

3. The method of claim 2 wherein said flows of air are directed horizontally of said containers.

4. The method of claim 1 wherein said plurality of containers are stacked within said incubation chamber in a plurality of vertically spaced apart rows.

5. The method of claim 4 wherein said environment is maintained at 99% relative humidity, 5% carbon dioxide content, and a fluctuating temperature of from 85° F. to 90° F. during said step of incubating.

6. The method of claim 5 wherein said flows of air are directed into said closed incubation chamber laterally of said containers.

7. The method of claim 6 wherein said flows of air are directed horizontally of said containers.

8. The method of claim 1 wherein said flows of air are pulsed during said step of incubating.

9. The method of claim 1 wherein said flows of air contain a carbon dioxide content of at least 5% to 7% by volume.

10. The method of claim 1, wherein the fungal mycelium comprises aerial mycelium.

11. The method of claim 10, wherein said flows of air provide a directed force that modulates the structure of the aerial mycelium.

12. The method of claim 1, wherein passing said flows of air over the growth media in each said container comprises passing said flows of air across the surface of the growth media in each said container.

13. The method of claim 1, wherein the mycelium biopolymer consisting essentially of fungal mycelium is a panel of mycelium biopolymer consisting essentially of fungal mycelium.

14. The method of claim 1, further comprising passing said flows of air over growing mycelium in each said container.

15. The method of claim 1, wherein the containers are not outfitted with lids.

16. The method of claim 1, further comprising distributing a mist through said incubation chamber for passage over the growth media in each said container.

17. The method of claim 16, wherein the mist contains moisture and a solute.

18. The method of claim 16, wherein aerial hyphae grow out of each said container during said incubation time period, and said mist is distributed at regulated amounts onto a top surface of said aerial hyphae.

* * * * *